(12) United States Patent
Takemura et al.

(10) Patent No.: US 7,045,363 B2
(45) Date of Patent: May 16, 2006

(54) NUCLEIC ACID-BOUND POLYPEPTIDE METHOD OF PRODUCING NUCLEIC ACID-BOUND POLYPEPTIDE AND IMMUNOASSAY USING THE POLYPEPTIDE

(75) Inventors: Fuminori Takemura, Higashiyamato (JP); Eiichi Ueno, Hino (JP); Satoru Itoh, Machida (JP)

(73) Assignee: Fujirebio Inc., Tokyo (JP)

( * ) Notice: Subject to any disclaimer, the term of this patent is extended or adjusted under 35 U.S.C. 154(b) by 0 days.

(21) Appl. No.: 09/306,780

(22) Filed: May 7, 1999

(65) Prior Publication Data

US 2001/0051336 A1 Dec. 13, 2001

Related U.S. Application Data

(62) Division of application No. 08/841,657, filed on Apr. 30, 1997, now abandoned.

(30) Foreign Application Priority Data

May 1, 1996 (JP) .............................. 8-134444

(51) Int. Cl.
- *G01N 33/55* (2006.01)
- *G01N 33/566* (2006.01)
- *C12Q 1/00* (2006.01)
- *C12Q 1/68* (2006.01)
- *C12N 11/00* (2006.01)

(52) U.S. Cl. ............................ 436/501; 422/72; 435/4; 435/6; 435/7.1; 435/69.3; 435/69.7; 435/174; 435/402; 435/403; 436/518; 436/523; 436/533; 436/534; 436/807; 436/824

(58) Field of Classification Search .................. 422/73; 435/4, 6, 7.1, 69.3, 69.7, 174, 402, 403; 46/501, 46/518, 523, 533, 534, 807, 824; 424/134.1, 424/185.1, 192.1; 436/501, 506, 514, 518, 436/526, 533, 548; 530/396
See application file for complete search history.

(56) References Cited

U.S. PATENT DOCUMENTS

| | | | | |
|---|---|---|---|---|
| 4,722,840 A | * | 2/1988 | Valenzuela et al. | ........... 424/88 |
| 4,749,647 A | * | 6/1988 | Thomas et al. | ................. 435/6 |
| 4,829,011 A | * | 5/1989 | Gibbons | ..................... 436/512 |
| 5,670,152 A | * | 9/1997 | Weiner et al. | ........... 424/189.1 |

FOREIGN PATENT DOCUMENTS

| | | | |
|---|---|---|---|
| EP | 0 286 239 | | 10/1988 |
| EP | 0704221 A | * | 9/1994 |
| EP | 0704 221 A2 | | 9/1994 |
| JP | 6-27109 | | 2/1994 |
| JP | 7-118291 | | 5/1995 |
| WO | WO 91/12328 | | 8/1991 |
| WO | WO 93/14768 | * | 1/1993 |

*Primary Examiner*—Lynette R. F. Smith
*Assistant Examiner*—J. Hines
(74) *Attorney, Agent, or Firm*—Oblon, Spivak, McClelland, Maier & Neustadt, P.C.

(57) ABSTRACT

A nucleic acid-bound polypeptide produced by binding a nucleic acid to a polypeptide, a method of producing the nucleic acid-bound polypeptide, and applications of the nucleic acid-bound polypeptide, including immunoassays for an antigen or antibody, such as an agglutination immunoassay are provided.

3 Claims, 2 Drawing Sheets

OTHER PUBLICATIONS

Gailbert et al. 1979. Nucleotide sequence of the hepatitis B virus genome (subtype ayw) cloned in E. coli. Nature. 281: 646–650. 1979.*

Pasek et al. 1979. Hepatitis B virus genes and their expression in E. coli. Nature. 282: 575–579. 1979.*

Ono et al. 1983. The complete nucletide sequences of the cloned hepatitis B virus DNA; subtype adr and adw. Nucleic Acdis Research. 11: No. 6, 1747–1757. 1983.*

Fujiyama et al., 1983. Cloning and structural analyses of hepatitis B virus DNAs, subtype adr. Nucleic Aids Research. 11: No. 13, 4601–4610. 1983.*

Kobayashi et al. 1984. Complete nucleotide sequence of hepatitis B virus DNA of subtype adr and its conserved gene organization. Gene. 30: 227–232. 1984.*

Okamoto et al. 1988. Typing Hepatitis B Virus by Homology by in Nucleotide Sequence: Comparision of Surface Antigen Subtypes. J. Gen. Virol. 69: 2575–2583. 1988.*

Birnbaum et al. 1990. Hepatitis B vVrus Nucleocapsid Assembly: Primary Structure Requirements in the Core Protein. J. of Virology. 64: No. 7, 3319–3330. 1990.*

R. Caswell et al., "Attempts to Engineer an Escherichia Coli DNA–Binding Protein as a Tool for Affinity Purification of Heterologous Proteins," *Biotechnology Techniques*, vol. 7, No. 4, (Apr. 1993), pp. 307–312.

Gailbert et al, "Nucleotide Sequence of the Hepatitis B Virus Genome (Subtype AYW) Cloned in E. Coli," Nature, 281: 646–650 (1979).

Pasek et al, "Hepatitis B Virus Genes and Their Expression in E. Coli", Nature 282:575–579.

Ono et al, "The Complete Nucleotide Sequence of the Cloned Hepatitis B Virus DNA: Sutype ADR and ADW.", Nucleic Acids. Research, 11:No. 13, 4601–4610 (1983).

Kobayashi et al, "Complete Nucleotide Sequence of Hepatitis B Virus DNA of Subtype ADR and its Conserved Gene Organization", Gene. 30:227–232 (1984).

Okamoto et al, "Typing Hepatitis B Virus by Homology in Nucleotide Sequence: Comparison of Surface Antigen Subtypes", J. Gen. Virol. 69:2575–2583 (1988).

Birnbaum et al, "Hepatitis BI Virus Nucleocapsid Assembly: Primary Structure Requirements in the Core Protein", J. of Virology 64:No. 7, 3319–3330 (1990).

* cited by examiner

NUCLEIC ACID-BOUND POLYPEPTIDE METHOD OF PRODUCING NUCLEIC ACID-BOUND POLYPEPTIDE AND IMMUNOASSAY USING THE POLYPEPTIDE

CROSS-REFERENCE TO RELATED APPLICATIONS

This application is a Divisional Application of U.S. application Ser. No. 08/841,657 filed Apr. 30, 1997 (now abandoned), which claims priority to Japanese Patent Application No. 8-134444 filed May 1, 1996.

BACKGROUND OF THE INVENTION

1. Field of the Invention

The present invention relates to a nucleic acid-bound polypeptide, a method of producing the nucleic acid-bound polypeptide, and an immunoassay using the nucleic acid-bound polypeptide.

2. Discussion of Background

Various studies have been made as to how to maintain the specific steric structure of a combinant protein produced by gene engineering, more specifically gene manipulation, and also as to how to apply the thus produced protein to an antigen-antibody reaction.

In the production of the combinant protein, in particular, in the course of a purification step of the produced protein, a denaturation operation is inevitably carried out. In such purification step, it is not always possible to maintain a natural structure of the protein, so that such protein cannot be used in an immunoassay system.

Various factors are also known that affect reactions which are peculiar to each of various assays. It is known that for these reasons or other, the above-mentioned antigen-antibody reaction does not always proceed as desired when the combinant protein is used.

For example, there is known an agglutination immunoassay as one of immunoassays. For instance, when an antibody corresponding to an antigen is assayed by agglutination immunoassay, the antigen is fixed on the surface of particles such as latex particles, and such antigen-fixed particles are allowed to react with the antibody in a test sample. When the antibody is present in the test sample, the antigen-fixed particles agglutinate due to the antigen-antibody reaction, so that, for instance, the absorbance of the test sample changes. Therefore by measuring the absorbance of the test sample, the degree of the agglutination can be determined, and accordingly the antibody in the test sample can be quantitatively measured from the measured absorbance of the test sample.

However, when the recombinant protein is used as the antigen to be fixed on the surface of the particles in the above-mentioned agglutination immunoassay, it occasionally occurs that even though the protein itself has reactivity with the antibody to be assayed and the antibody is in fact present in the test sample, no agglutination takes place.

Conventionally, in the case where no agglutination takes place as mentioned above, the recombinant protein is modified or expressed in the form of a fused protein in order to improve the agglutination reactivity of the protein. However, it is extremely difficult to modify the protein so as to impart the desired properties thereto, while maintaining the antigenicity (i.e. the reactivity with the antibody).

Furthermore, the recombinant protein is often of an insoluble kind, so that when the thus produced protein is purified, the protein has to be subjected to solubilization treatment. However, the protein is often denatured in the course of the purification treatment, losing the necessary antigenicity.

Therefore, it is preferable that a soluble protein be directly produced by genetic engineering.

SUMMARY OF THE INVENTION

It is therefore a first object of the present invention to provide a modified polypeptide, which is modified so as to change the properties of polypeptide such as the isoelectric point, the molecular weight and the three-dimensional structure thereof, but without changing the antigenicity thereof.

A second object of the present invention is to provide a method of producing the above-mentioned recombinant polypeptide in such a manner that the produced polypeptide can be obtained in a soluble fraction.

A third object of the present invention is to provide an immunoassay for assaying an antigen comprising a polypeptide, which is conventionally difficult to perform.

The first object of the present invention can be achieved by a nucleic acid-bound polypeptide which is produced by binding a nucleic acid to a polypeptide.

In the above nucleic acid-bound polypeptide, the nucleic acid may be bound to at least one terminus of the polypeptide.

The nucleic acid-bound polypeptide may further comprise a nucleic acid-binding motif through which the nucleic acid is bound to the polypeptide.

The above-mentioned polypeptide and the nucleic acid-binding motif may be expressed in the form of a fusion polypeptide by genetic engineering.

The nucleic acid-binding motif may have an amino acid sequence with sequence No. 2 defined in a sequence table attached to the specification of this application.

The above-mentioned polypeptide can be used as an antigen to be assayed by an immunoassay.

The second object of the present invention can be achieved by a method of producing a nucleic acid-bound polypeptide comprising the steps of:

producing a recombinant polypeptide, binding a nucleic acid to the recombinant polypeptide to produce a nucleic acid-bound polypeptide as a soluble fraction, and purifying the nucleic acid-bound polypeptide from the soluble fraction.

In the above-mentioned method of producing the nucleic acid-bound polypeptide, the step of binding the nucleic acid to the polypeptide to produce the nucleic acid-bound polypeptide may comprises the steps of:

fusing a gene which codes the polypeptide and a gene which codes the nucleic acid-binding motif to produce a fusion gene, and expressing the fusion gene to produce the nucleic acid-bound polypeptide via the nucleic acid-binding motif.

The third object of the present invention can be achieved by an immunoassay for assaying an antigen comprising a polypeptide, or an antibody corresponding to the polypeptide, using as an antigen for the immunoassay the above-mentioned nucleic acid-bound polypeptide.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
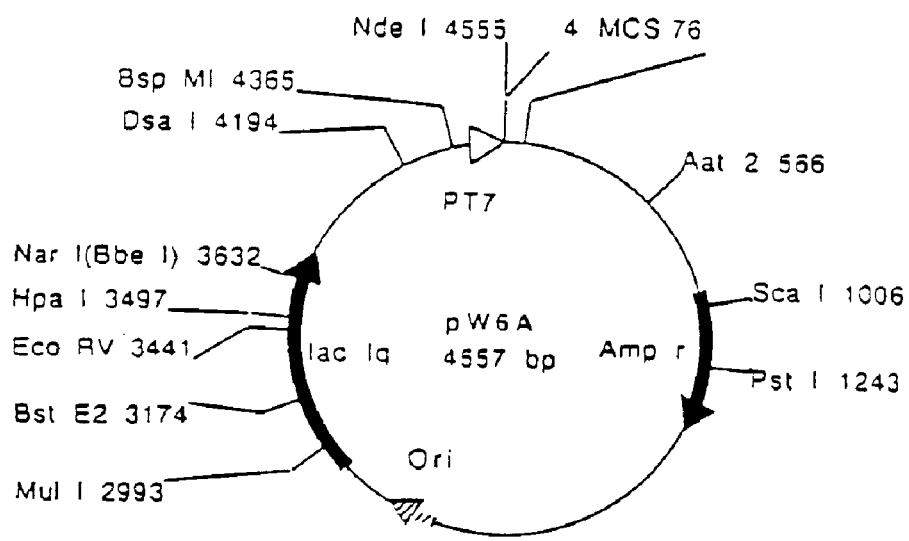
FIG. 1 is a genetic map of a cloning vector pW6A for use in expressing HCV core protein used in examples of the present invention.

The nucleic acid-bound polypeptide of the present invention can be provided by binding a nucleic acid to a polypeptide, whereby the properties of the polypeptide, such as the isoelectric point, the molecular weight and the three-dimensional structure thereof, can be changed without the antigenicity thereof being changed.

As the "polypeptide" for use in the present invention, any polypeptide can be employed as long as the polypeptide itself exhibits antigenicity and therefore the number of amino acid residues which constitute the polypeptide is 6 or more. It is preferable that the number of the amino acid residues which constitute the "polypeptide" for use in the present invention be 8 or more.

Examples of the "polypeptide" for use in the present invention include composites of a polypeptide and another component or other components such as sugar or lipid, namely glycoprotein and lipo protein.

There is no particular limitation to the size of the nucleic acid which is bound to the polypeptide as long as the nucleic acid can change the above-mentioned properties of the polypeptide, such as isoelectric point, molecular weight and three-dimensional structure, without changing the antigenicity thereof. Normally, the number of bases of the nucleic acid for use in the present invention is 100 b to 10 kb, preferably about 1 kb to 5 kb.

Furthermore, the nucleic acid to be bound to the polypeptide may be either DNA or RNA. In the present invention, there is no limitation to the nucleotide sequence to be bound to the polypeptide. Any nucleotide sequence is acceptable for use in the present invention.

The nucleic acid may be bonded to any portion of the polypeptide. For instance, the nucleic acid may be bonded to the N-terminus or the C-terminus of the polypeptide, but the bonding is not limited to such terminus. In the present invention, the nucleic acid may be either directly or indirectly bonded to the polypeptide. For instance, the nucleic acid may be bonded to the polypeptide via a nucleic acid-binding motif which is also a polypeptide.

In this application, with respect to the binding of the nucleic acid to the polypeptide, the term "binding" or "bound" means all kinds of chemical bondings between the polypeptide and the nucleic acid with attractive force in a wide range of relatively weak attractive force to strong attractive force, without any particular limitation to the bonding mode, including the so-called association, covalent bonding, ionic bonding, coordinate bonding, and hydrogen bonding.

In the present invention, when the nucleic acid-bound polypeptide is produced by genetic engineering, the nucleic acid-bound polypeptide may be expressed in the form of a polypeptide to which the nucleic acid is bound, thereby producing the nucleic acid-bound polypeptide.

Alternatively, after a recombinant polypeptide is expressed, the nucleic acid may be bound to the recombinant polypeptide, thereby producing the nucleic acid-bound polypeptide.

To be more specific, when a polypeptide is expressed as a fusion polypeptide, with a nucleic acid-binding motif which is known to have a function of binding the nucleic acid to the polypeptide being included in the function of the polypeptide to be expressed, a polypeptide with the nucleic acid-binding motif is expressed, and the nucleic acid in the host is simultaneously bound to the recombinant polypeptide via the nucleic acid-binding motif, so that the nucleic acid-bound polypeptide can be produced. This nucleic acid-bound polypeptide can be purified thereafter.

Alternatively, the nucleic acid-bound polypeptide can be obtained by reconstituting the polypeptide by mixing the expressed polypeptide with the nucleic acid.

In connection with the above-mentioned nucleic acid-binding motif, various nucleic acid-binding motifs are known. For example, in J. of Virology, 64 3319–3330 (1990), there is reported a nucleic acid-binding motif which is present in HBc protein amino acid sequence of hepatitis B virus (HBV), and in Biochim. Biophys. Act, 950, 45–53 (1988), there is reported protamin, which is a nucleic acid-bound protein in mouse. These can also be employed in the present invention.

The nucleotide sequence and the amino acid sequence of the nucleic acid-binding motif of HBc are respectively shown in the sequence No. 1 and the SEQ ID NO. 2 in the sequence table attached to this specification; and the nucleotide sequence and the amino acid sequence of the mouse protamine are respectively shown in the sequence No. 17 and the SEQ ID NO. 18 in the sequence table attached to this specification As mentioned above, when the protein or polypeptide conventionally produced by genetic engineering is used as the antigen to be fixed on the surface of the particles in the conventional agglutination immunoassay, it occasionally occurs that even though the polypeptide itself has reactivity with the antibody to be assayed and the antibody is in fact present in the test sample, no agglutination takes place.

In the present invention, however, this conventional problem is completely solved by use of the nucleic acid-bound polypeptide. Namely, when the nucleic acid-bound polypeptide of the present invention is used as the antigen to be fixed on the surface of particles for use in the agglutination immunoassay, the agglutination successfully takes place proportionally in accordance with the amount of the corresponding antibody in the test sample.

The nucleic acid-bound polypeptide of the present invention can be applied not only to the above-mentioned agglutination, but also to any conventional immunoassay such as ELISA (enzyme-linked immunosorbent assay).

In the present invention, when the antibody in a test sample is assayed, the nucleic acid-bound polypeptide may be fixed as the corresponding antigen, for example, on the surface of solid particles and is allowed to react with the antibody in the test sample, so that the amount of the antibody in the test sample is measured as corresponding to the amount of the antibody which has reacted with the nucleic acid-bound polypeptide fixed as the corresponding antigen on the surface of solid particles.

Furthermore, in the present invention, an antigen comprising a polypeptide can also be assayed. In this assay system, the nucleic acid-bound polypeptide may also be fixed, for example, on the surface of solid particles. An antigen in the test sample comprises the same polypeptide as in the nucleic acid-bound polypeptide. In this assay system, the nucleic acid-bound polypeptide fixed on the solid particles and the antigen in the test sample are both present as antigens. When an antibody corresponding to the antigen in the test sample is added in the form of an antibody agent to this assay system, there occur competition antigen/antibody reactions between the antigen in the test sample and the antibody in the agent, and between the nucleic acid-bound polypeptide fixed on the solid particles and the antibody in the agent. In other words, the reaction between the nucleic acid-bound polypeptide and the antibody in the agent is hindered to some degree by the reaction between the antigen in the test sample and the antibody in the agent, namely by the presence of the antigen in the test sample. From the degree of the reaction hindrance, the amount of the antigen in the test sample can be assayed.

Thus, the polypeptide antigen in a test sample can also be assayed by carrying out the above-mentioned competition reaction with the addition of a known amount of the nucleic acid-bound polypeptide to the test sample.

Conventionally, when polypeptide is produced by genetic engineering, in many cases, the recombinant polypeptide is obtained as an insoluble fraction. Therefore, when the thus obtained polypeptide is used in practice, the polypeptide must be subjected to solubilization treatment. However, the polypeptide is often denatured in the course of the solubilization treatment, changing the antigenicity. Therefore it is preferable that the recombinant polypeptide be obtained as a soluble fraction.

In the method of producing the nucleic acid-bound polypeptide of the present invention, for example, a polypeptide is produced by genetic engineering, and the thus produced polypeptide is simultaneously caused to be bound to a nucleic acid in the host, whereby the nucleic acid-bound polypeptide is obtained as a soluble fraction.

Furthermore, as shown in the following examples, for example, when the polypeptide to be expressed is expressed as a fused polypeptide of a polypeptide and a nucleic acid-binding motif of HBc, the nucleic acid is bound to the nucleic acid-binding motif at the same time as the expression thereof, so that the nucleic acid-bound polypeptide is obtained in the soluble fraction.

Thus, there can be attained the method of producing the nucleic acid-bound polypeptide of the present invention, which comprises the steps of producing the recombinant polypeptide, binding the nucleic acid to the polypeptide to produce the nucleic acid-bound polypeptide as a soluble fraction, and purifying the nucleic acid-bound polypeptide from the soluble fraction.

Other features of this invention will become apparent in the course of the following description of exemplary embodiments, which are given for illustration of the invention and are not intended to be limiting thereof.

REFERENCE EXAMPLE 1

[Expression of HCV Core Protein (1–120aa)]

A DNA fragment for coding the HCV core polypeptide with SEQ ID NO. 3 in the attached sequence table was amplified by the PCR (Polymerase Chain Reaction) method, using as a template molecule a plasmid CKSC1150 with a DNA fragment including an HCV core region, and was then digested with a restriction endonuclease EcoRI and a restriction endonuclease BamHI.

An HCV core region-including DNA fragment 370 bp was separated by 1% agarose gel electrophoresis. This DNA fragment was inserted into an EcoRI-BamHI site of an expression plasmid pW6A shown in FIG. 1, so that a plasmid pW6AHCV core 120 was prepared.

By use of this plasmid, *Escherichia coli* BL21 (DE3) (obtained from Brookhaven National Laboratory) was subjected to transformation, so that an ampicillin-resistant transformed *Escherichia coli* BL21 (DE3)/pW6AHCV core 120 for expressing HCV core polypeptide 120 was obtained, and an HCV core protein (1–120 aa) was expressed. Hereinafter, the thus expressed protein is referred to as "120". The nucleotide sequence of "120" and the amino acid sequence of "120" are respectively shown in SEQ ID NO. 3 and SEQ ID NO. 4 in the sequence table attached to this specification.

EXAMPLE 1

[Preparation of Plasmid]

A DNA fragment for coding HCV core polypeptides 150 and 120 which are respectively shown with SEQ ID NO. 5 and with SEQ ID NO. 3 in the attached sequence table was amplified by the PCR (Polymerase Chain Reaction) method, using as a template molecule a plasmid CKSC1150 with a DNA fragment including a HCV core region being introduced, and was then digested with a restriction endonuclease EcoRI and a restriction endonuclease BamHI.

An HCV core region-including DNA fragment 470 bp and an HCV core region-including DNA fragment 370 bp were separated by 1% agarose gel electrophoresis. These DNA fragments were inserted into an EcoRI-BamHI site of the expression plasmid pW6A shown in FIG. 1, whereby a plasmid pW6AHCV core 150 and a plasmid pW6AHCV core 120 were prepared.

A DNA fragment for coding an HBc nucleic acid-binding motif shown with SEQ ID NO. 1 in the sequence table attached to this specification was amplified by the PCR (Polymerase Chain Reaction) method, using as a template molecule a plasmid pHBV-11 (Nucleic Acids Res., 18, 4587 (1990)), and was then digested with the BamHI.

A DNA fragment 110 bp including a nucleic acid-binding motif was separated by 2% agarose gel electrophoresis. This DNA fragment was inserted into an EcoRI-BamHI site of each of the above-mentioned plasmid pW6AHCV core 150 and plasmid pW6AHCV core 120.

By use of these plasmids, *Escherichia coli* BL21 (DE3) (obtained from Brookhaven National Laboratory) was subjected to transformation, so that an ampicillin-resistant transformed *Escherichia coli* BL21 (DE3)/pW6AHCV core 150NA and an ampicillin-resistant transformed *Escherichia coli* BL21 (DE3)/pW6AHCV core 120NA were obtained.

In this specification, the proteins to which the nucleic acid-binding motif is bound for expressing the above-mentioned transformed *Escherichia coli* BL21 (DE3)/pW6AHCV core 150NA and the above-mentioned transformed *Escherichia coli* BL21 (DE3)/pW6AHCV core 120NA are respectively referred to as "150NA" and "120NA".

The nucleotide sequence of "150NA" and the amino acid sequence of "150NA" are respectively shown in SEQ ID NO. 9 and Sequence ID. No. 10 in the sequence table attached to this specification; and the nucleotide sequence of "120NA" and the amino acid sequence of "120NA" are respectively shown in SEQ ID NO. 7 and SEQ ID NO. 8 in the sequence table attached to this specification.

EXAMPLE 2
[Expression of Recombinant Protein (150NA and 120NA)]

Each of the transformed *Escherichia coli* BL21 (DE3)/pW6AHCV core 150 and the transformed *Eacherichia coli* BL21 (DE3)/pW6AHCV core 120 prepared in Example 1 was separately cultured overnight in 2 ml of an LB culture medium containing 50 µg/ml of ampicillin at 37° C.

After the optical density (OD) of each culture medium reached to 0.6 to 0.8 with a light with a wavelength of 600 nm by preculture, expression induction was carried out with the addition of 0.5 mM IPTG (Isopropyl-β-D(−)-thiogalactopyranoside) thereto, and the cultivation was continued for another two hours.

1.5 ml of the *Eacherichia coli* cultivation medium was centrifuged at 5000 rpm for 2 minutes, whereby the *Escherichia coli* was collected. The thus collected *Escherichia coli* was suspended in 100 µl of a buffer solution (10 mM tris-HCl, pH 8.0, 0.1 M NaCl, 1 mM EDTA), and was then subjected to ultrasonic disruption for 15 minutes, whereby the *Escherichia coli* was completely disrupted, whereby two test samples, namely an *Escherichia coli* test sample of *Escherichia coli* BL21 (DE3)/pW6AHCV core 150NA and an *Escherichia coli* test sample of *Escherichia coli* BL21 (DE3)/pW6AHCV core 120NA, were prepared.

8 µl of a three-times concentration SDS polyacrylamide buffer solution (0.15 M tris-HCl, pH 6.8, 6% SDS, 24% glycerol, 6 mM EDTA, 2% 2-mercaptoethanol, 0.003% bromophenol blue) was added to each of the above test samples separately. Each mixture was then stirred sufficiently and was subjected to SDS-polyacrylamide gel electrophoresis.

Western blotting was performed on a nitrocellulose filter, using each of the thus prepared test samples. After performing blocking using 1% BSA, each of the test samples was allowed to react with an HCV core antibody human serum which was diluted 200 times with a phosphoric acid buffer solution (10 mM phosphoric acid, pH 7.4, 0.15 M NaCl). Furthermore, a peroxydase enzyme labeled anti-human IgG rabbit polyclonal antibody (made by Daco Co., Ltd.) was then allowed to react therewith. After washing, 10 ml of a substrate coloring liquid (0.01% aqueous solution of hydrogen peroxide, 0.6 mg/ml 4-chloro-1-naphthol) was added thereto, whereby each test sample was colored.

Figure 2:
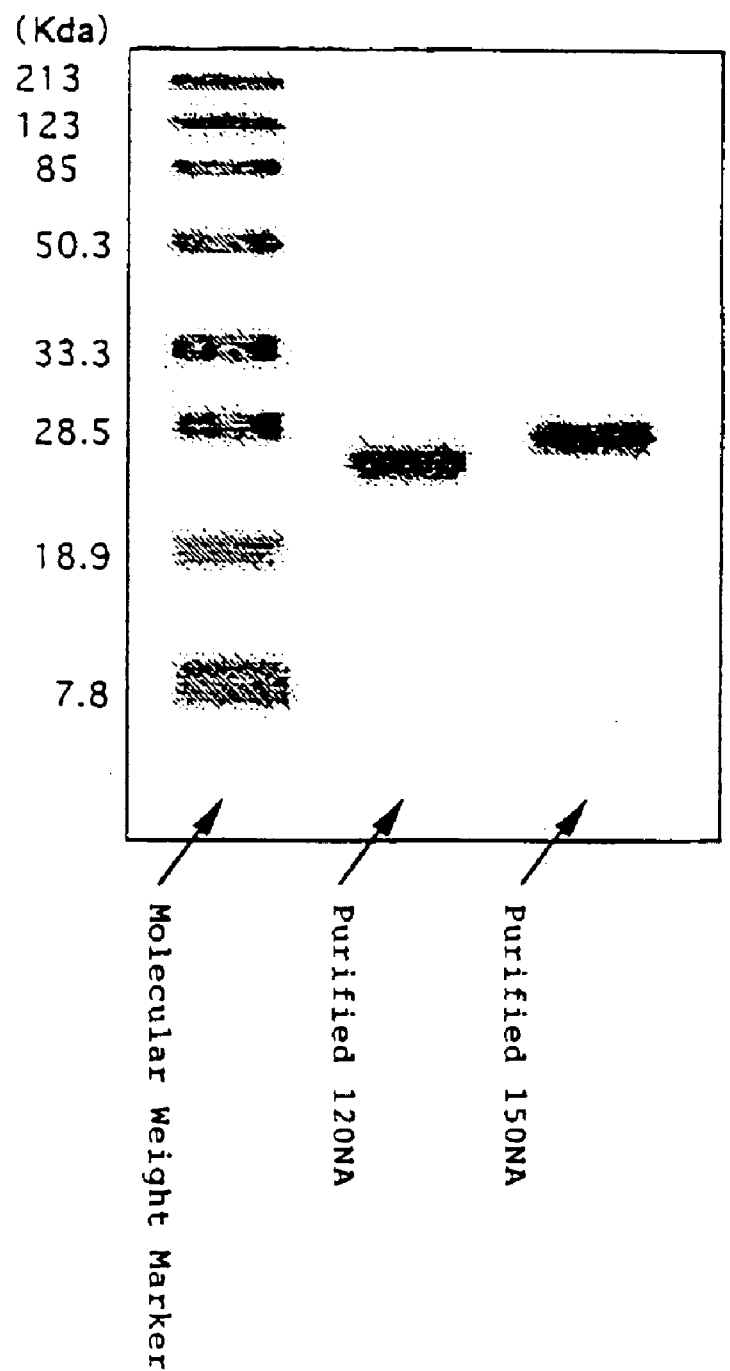
FIG. 2 is a diagram showing the results of Western blotting performed for showing the reactivity of a HCV core protein prepared by genetic engineering in an example of the present invention with HCV core positive human serum.

The results are shown in FIG. 2. As shown in FIG. 2, both the *Escherichia coli* test sample of *Escherichia coli* BL21 (DE3)/pW6AHCV core 150 NA and the *Escherichia coli* test sample of *Escherichia coli* BL21 (DE3)/pW6AHCV core 120NA exhibited a positive reaction with the HCV core antibody human serum.

EXAMPLE 3
[Purification of Soluble Nucleic Acid-bound 120NA Recombinant Protein (120(+))]

The *Escherichia coli* BL21 (DE3)/pW6AHCV core 120NA prepared in Example 1 was cultured overnight in an LB culture medium at 37° C. The optical density (OD) of the culture medium was adjusted by preculture so as to be about 0.7 when measured with light with a wavelength of 600 nm. Expression induction was then carried out with the addition of 0.5 mM IPTG thereto, and thereafter the cultivation was continued for two hours and 30 minutes.

The *Escherichia coli* cultivation medium was centrifuged, whereby the *Escherichia coli* was collected. To the thus collected *Escherichia coli*, 150 ml of a buffer solution (50 mM tris-HCl, pH 8.0, 20% ethanol, 0.2 M NaCl, 0.3% octylthioglucoside (hereinafter referred to as "OTG") was added, and the mixture was ice-cooled and subjected to ultrasonic disruption.

This mixture was then centrifuged, whereby a soluble fraction which contained therein a nucleic acid-bound 120NA (hereinafter referred to as "120NA(+)") was recovered.

A 50%-sucrose concentration buffer solution was prepared by adding sugar to a buffer solution (50 mM tris-HCl, pH 8.0, 20% ethanol) in such a manner that the concentration of sucrose in the buffer solution was 50%. In the same manner as mentioned above, a 30%-sucrose concentration buffer solution, and a 20%-sucrose concentration buffer solution were prepared.

These buffer solutions were overlaid in an ultracentrifuge tube in the direction from the bottom to the top portion of the tube in the order of the 50% sucrose concentration buffer solution, the 30%-sucrose concentration buffer solution and the 20%-sucrose concentration buffer solution.

The 120NA(+) containing soluble fraction was overlaid on top of the overlaid buffer solutions in the ultracentrifuge tube, and was then subjected to a first sucrose density gradient ultracentrifugation at 10° C., with a centrifugal force of 100,000 g, for 12 hours, using a Beckman ultrasonic centrifuge.

The 120NA(+) was recovered in a portion with a sucrose concentration of about 30 to 40%.

The 120NA(+) containing fraction recovered by the first sucrose density gradient ultracentrifugation was purified by Superdex 200 (gel filtration column) (made by Pharmacia Co., Ltd.) which was equilibrated with a buffer solution (0.3 M NaCl, 0.1% myristyl sulfobetaine (Trademark "SB3-14" made by Sigma Co., Ltd.), whereby 120NA(+) with a molecular weight of about 700 to 1000 kDa was recovered.

A 50%-sucrose concentration buffer solution was prepared by adding sucrose to a buffer solution (50 mM tris-HCl, pH 8.0, 20% ethanol) in such a manner that the concentration of sucrose in the buffer solution was 50%. In the same manner as mentioned above, a 20%-sucrose concentration buffer solution was prepared.

These buffer solutions were overlaid in an ultracentrifuge tube in the direction from the bottom to the top portion of the tube in the order of the 50% -sucrose concentration buffer solution and the 20%-sucrose concentration buffer solution.

The above-mentioned 120NA(+) with a molecular weight of about 700 to 1000 kDa was overlaid on top of the overlaid buffer solutions in the ultracentrifuge tube, and was then subjected to a second sucrose density gradient ultracentrifugation at 10° C., with a centrifugal force of 100,000 g, for 12 hours, using the Beckman ultrasonic centrifuge, whereby the 120NA(+) was concentrated and purified.

REFERENCE EXAMPLE 2
[Purification of Insoluble 120NA]

The *Escherichia coli* BL21 (DE3)/pW6AHCV core 120NA prepared in Example 1 was cultured overnight in an LB culture medium at 37° C. The optical density (OD) of the culture medium was adjusted by preculture so as to have about 0.7 when measured with light with a wavelength of 600 nm. Expression induction was then carried out with the addition of 0.5 mM IPTG thereto, and the cultivation was continued for two hours and 30 minutes.

The *Escherichia coli* cultivation medium was then centrifuged, whereby the *Escherichia coli* was collected. To the thus collected *Escherichia coli*, 150 ml of a buffer solution (50 mM tris-HCl, pH 8.0, 20% ethanol, 0.2 M NaCl, 0.3% OTG) was added, and the mixture was ice-cooled and subjected to ultrasonic disruption.

This mixture was then centrifuged, whereby an insoluble 120NA fraction was obtained. The thus obtained insoluble 120NA fraction was made soluble by a buffer solution (6M urea, 50 mM glycine-NaOH, pH 11.7) and was then subjected to centrifugation, whereby a supernatant fraction was obtained.

The thus obtained supernatant fraction was subjected to ion exchange purification, using an SFF cationic ion exchange column (made by Pharmacia Co., Ltd.) which was equilibrated with a buffer solution (6M urea, 50 mM glycine-NaOH, pH 11.7), with sodium chloride elution.

The SFF eluted fraction was then purified, using Superdex 200 (gel filtration column) (made by Pharmacia Co., Ltd.) which was equilibrated with a buffer solution (6M urea-0.5M NaOH, 50 mM tris-HCl, pH 9.6). Thus, a purified 120NA was obtained in a portion with a molecular weight of about 22 kDa.

EXAMPLE 4

[Confirmation of Properties of 120NA and 120NA (+)]

The OD 260/280 nm ratio of the 120NA(+) purified in Example 3 was measured. The result was that the OD 260/280 nm ratio of the 120NA(+) was about 2.0, which was greater than the OD 260/280 nm ratio of the 120NA. This indicated that at least the polypeptide and the nucleic acid coexist in the 120NA(+).

Furthermore, in the sucrose density gradient ultracentrifugation, the 120NA was mostly collected in the zero % sucrose concentration region, while the 120NA(+) was mostly collected in an about 30–40% sucrose concentration region. It is considered that this fact indicates that the density of the 120NA(+) is different from that of the 120NA.

The 120NA(+) was subjected to enzyme treatment, using DNase or RNase. When the 120NA(+) was subjected to enzyme treatment, using RNase, the nucleic acid contained in the 120NA(+) was decomposed in its entirety by the RNase. It is considered that this fact indicates that the constituent nucleic acid of the 120NA(+) is RNA.

The 120NA(+) was also subjected to isoelectric focusing. The isoelectric point of the 120NA(+) was present in a wide range of pI 3.5 to 5.0.

In sharp contrast to this, the isoelectric points of the 120NA purified in Reference Example 2 was pI 12.84, with a strong positive charge, which was significantly different from the isoelectric point of the 120NA(+).

Furthermore, the 120NA(+) was also subjected to Native electrophoresis, using a 3% agarose 3% polyacrylamide gel. From the fact that luminescence was observed at the time of Ethidium bromide stain of the 120NA(+), it was confirmed that the nucleic acid was contained in the 120NA(+).

The 120NA(+) was further subjected to Western blotting and Coomassie Brilliant Blue stain, using the same gel as used in the above-mentioned Ethidium Bromide stain. The result was that in the Western blotting, the reactivity of the 120NA(+) with an anti-HCV core antibody was observed at the same position as that of the portion made luminescent by the Ethidium Bromide stain; and in the Coomassie Brilliant Blue stain, the presence of the polypeptide was confirmed.

In sharp contrast to this, with respect to the 120A, the transfer of the 120NA into the gel was not confirmed in the Native electrophoresis even when the Western blotting and the Coomassie Brilliant Blue stain were carried out.

Thus, the properties of the 120NA(+) are entirely different from those of the 120NA with respect to the apparent molecular weight, the density, and the electric charge thereof, particularly because of the increase of the apparent molecular weight of the 120NA(+) due to the binding of the nucleic acid to the polypeptide in the 120NA(+), but there are no differences in the Western blotting and agglutination reactions between the two. From these facts, it is considered that the antigenicity is maintained in the 120NA(+).

REFERENCE EXAMPLE 3

[Expression of Lysine-fused 120 (120K10)]

In the same manner as in Example 1, pW6AHCV core 120 was subjected to such gene manipulation that 10 lysine residues were continuously fused to the C-terminus of pW6AHCV core 120, whereby pW6AHCV core 120K10 was prepared.

By use of this pW6AHCV core 120K10, *Escherichia coli* BL21 (DE3) was subjected to transformation, whereby an ampicillin-resistant transformed *Escherichia coli* BL21 (DE3)/pW6AHCV core K10 was obtained. Hereinafter, the protein expressed by this ampicillin-resistant transformed *Escherichia coli* BL21 (DE3)/pW6AHCV core K10 is referred to as 120K10.

The above transformed *Escherichia coli* BL21 (DE3)/pW6AHCV core K10 was cultured overnight in an LB culture medium at 37° C. The optical density (OD) of the culture medium was adjusted by preculture so as to have about 0.7 when measured with light with a wavelength of 600 nm. Expression induction was then carried out with the addition of 0.5 mM IPTG thereto, and the cultivation was continued for two hours and 30 minutes.

The *Escherichia coli* cultivation medium then was centrifuged, whereby the *Escherichia coli* was collected. To the thus collected *Escherichia coli*, 150 ml of a buffer solution (50 mM tris-HCl, pH 8.0, 20% ethanol, 0.2 M NaCl, 0.3% OTG) was added, and the mixture was ice-cooled and subjected to ultrasonic disruption.

This mixture was then centrifuged, whereby a soluble 120K10 fraction and an insoluble 120K10 fraction were separately obtained.

A 50%-sucrose concentration buffer solution was prepared by adding sucrose to a buffer solution (50 mM tris-HCl, pH 8.0, 20% ethanol) in such a manner that the concentration of sucrose in the buffer solution was 50%. In the same manner as mentioned above, a 30%-sucrose concentration buffer solution and a 20%-sucrose concentration buffer solution were prepared.

These buffer solutions were overlaid in an ultracentrifuge tube in the direction from the bottom to the top portion of the tube in the order of the 50%-sucrose concentration buffer solution, the 30%-sucrose concentration buffer solution and the 20%-sucrose concentration buffer solution.

The above-mentioned soluble 120K10 fraction was overlaid on top of the overlaid buffer solutions in the ultracentrifuge tube, and was then subjected to a sucrose density gradient ultracentrifugation at 10° C., with a centrifugal force of 100,000 g, for 12 hours, using the Beckman ultrasonic centrifuge. The 120K10 was not recovered in any of the 50%-sucrose concentration buffer solution, the 30%-sucrose concentration buffer solution and the 20%-sucrose concentration buffer solution, but was recovered on the top layer portion in the tube.

The above-mentioned insoluble 120K10 fraction was purified in the same manner as in Reference Example 2, using the SFF cationic ion exchange column (made by Pharmacia Co., Ltd.) and performing the gel filtration, whereby a purified 120K10 was recovered in a portion with a molecular weight of about 20 kDa.

REFERENCE EXAMPLE 4

[Assay of HCV Core Antigen Positive Serum]

The reactivity of each of HCV antibody positive serum 1 and HCV antibody positive serum 2 with a commercially available HCV antibody assay agent (Trademark "RIBA HCV 3.0 STRIP IMMUNOBLOT ASSAY" made by Chiron Co., Ltd.), using HCV antigen c100 (Amino acid Nos. 1569–1931), HCV antigen c33c (Amino acid Nos. 1192–1457), core antigen c22 (Amino acid Nos. 2–120) and NS5 (Amino acid Nos. 2054–2995). The result was that both HCV antibody positive serum 1 and HCV antibody positive serum 2 have antibodies in the entire antigen region including the core antigen region.

TABLE 1

Reactivity Tests of Positive Serums

|  | c100 | c33c | Core Antigen | NS5 | Judgement |
|---|---|---|---|---|---|
| Positive Serum 1 | 4+ | 4+ | 4+ | 4+ | Positive |
| Positive Serum 2 | 4+ | 4+ | 4+ | 4+ | Positive |

EXAMPLE 5

Each of the HCV antigens obtained in Reference Examples 1, 2, 3 and Example 3 was fixed on the surface of gelatin particles (made by Fujirebio Co., Ltd.) with a concentration of 10 mg/ml in a buffer solution (0.15M PBS, pH 7.1).

By use of HCV antibody positive serum 1 and HCV antibody positive serum 2 confirmed as having antibodies in the entire antigen region including the core antigen region in Reference Example 4, and a monoclonal antibody #2–7 obtained by subjecting HCV core antigen c22 to immunization, the immune reactivity of each of the above-mentioned HCV antigens fixed on the surface of gelatin particles was investigated.

25 µl of each HCV antigen-fixed gelatin particles and 25 µl of one of the above-mentioned HCV antibody positive serum 1 or HCV antibody positive serum 2, or 25 µl of the monoclonal antibody #2–7 were allowed to react in a microtiter plate (made by Fujirebio Co., Ltd.) for 2 hours, and agglutination images thereof were investigated. The results are shown in TABLE 2. In TABLE 2, the reactivity is shown with a dilution rate of $2^n$, and when a positive agglutination image was observed even when n was 4 or more in the dilution rate, the immune reactivity was judged as being "positive".

The monoclonal antibody #2–7 obtained by subjecting HCV core antigen c22 to immunization reacted with any HCV core antigen, but it was only the 120NA(+) fixed gelatin particles that HCV antibody positive serum 1 and HCV antibody positive serum 2 reacted in the above-mentioned reactions.

TABLE 2

Immune Reactivity Tests of HCV Core Antigens

| Name of Core Antigen | Positive Serum 1 | Positive Serum 2 | #2-7 |
|---|---|---|---|
| 120NA (+) | 6+ | 7 | 8 |
| 120NA | <3 | <3 | 7 |
| 120K10 | <3 | <3 | 6 |
| 120 | <3 | <3 | 4 |

EXAMPLE 6

Rearrangement of 120NA(+) from 120NA

By use of the transformed *Escherichia coli* BL21 (DE3)/pW6AHCV core 120NA prepared in Example 1, HCV core 120NA was purified from an insoluble fraction thereof in the same manner as in Reference Example 2. The molecular weight of the purified HCV core 120NA was about 22 kDa, and the OD 260/280 nm ratio thereof was about 0.7.

To the HCV core 120NA (hereinafter referred to as 120NA), a cyclic plasmid DNA (4.7 Kbp) derived from pW6A, 6M urea and 20% sucrose were added, and 120NA was dialyzed against a buffer solution (50 mM tris-HCL, 0.15M NaCl, 20% sucrose), whereby 120NA was rearranged to 120NA(+).

The 120NA(+) which was obtained by the above-mentioned dialysis and rearrangement was purified, using Superdex 200 (gel filtration column) (made by Pharmacia Co., Ltd.), whereby the 120NA(+) was recovered in a portion with a molecular weight of 700 to 1000 kDa.

A 50%-sucrose concentration buffer solution was prepared by adding sucrose to a buffer solution (50 mM tris-HCl, pH 8.0, 20% ethanol) in such a manner that the concentration of sucrose in the buffer solution was 50%. In the same manner as mentioned above, a 20%-sucrose concentration buffer solution was prepared.

These buffer solutions were overlaid in an ultracentrifuge tube in the direction from the bottom to the top portion of the tube in the order of the 50%-sucrose concentration buffer solution and the 20%-sucrose concentration buffer solution.

The above recovered 120NA(+) was overlaid on top of the overlaid buffer solutions in the ultracentrifuge tube, and was then subjected to a sucrose density gradient ultracentrifugation at 10° C., with a centrifugal force of 100,000 g, for 12 hours, using the Beckman ultrasonic centrifuge. The rearranged 120NA(+) was recovered in an about 40% to 50%-sucrose concentration portion of the buffer solution.

The OD 260/280 nm ratio of the 120NA before the rearrangement was about 0.7, and when the 120NA was rearranged to the 120NA(+), the OD 260/280 nm ratio thereof was changed from about 0.7 to about 1.7.

Furthermore, the above-mentioned rearranged 120NA(+) and the soluble 120NA(+) prepared in Example 3 have almost the same molecular weight after the gel filtration thereof, and also have almost the same specific weight thereof after the sucrose density gradient ultracentrifugation thereof. Thus, it is considered that these facts indicate that the above-mentioned rearrangement from the 120NA to the 120NA(+) was successfully conducted.

EXAMPLE 7

[Construction of Transformed *Escherichia coli* BL21 (DE3)/pW6AHCV Core 120NA120 for Expressing 120-fused 120NA (120NA120)]

A DNA fragment for coding an HCV core polypeptide shown with sequence ID. No. 3 in the attached sequence table was amplified by the PCR method, using as a template molecule a plasmid CKSC1150 with a DNA fragment including a HCV core region being introduced, and was then digested with a restriction endonuclease NheI and a restriction endonuclease EcoRI.

An HCV core region-including DNA fragment 370 bp was separated by 1% agarose gel electrophoresis. This DNA fragment was inserted into an NheI—EcoRI site of the expression plasmid pW6A shown in FIG. 1, whereby a plasmid pW6AHCV core 120 (NheI/EcoRI) was prepared.

A DNA fragment for coding the HCV core polypeptide shown with sequence ID. No. 3 in the attached sequence table was amplified by the PCR method, using as a template molecule a plasmid CKSC1150, and was then digeated with a restriction endonuclease EcoRI and a restriction endonuclease BamHI.

An HCV core region-including DNA fragment 370 bp was then separated by 1% agarose gel electrophoresis. This DNA fragment was inserted into an EcoRI-BamHI site of the plasmid pW6AHCV core 120 (NheI/EcoRI), whereby a plasmid pW6AHCV core 120-120 was prepared.

A DNA fragment for coding an HBc nucleic acid-binding motif with sequence ID. No. 1 in the attached sequence table was amplified by the PCR method, using as a template molecule a plasmid pHBV-11, and was then digested with a restriction endonuclease EcoRI.

A DNA fragment 110 bp including the nucleic acid-binding motif was separated by 2% agarose gel electrophoresis. This DNA fragment was inserted into an EcoRI site of the above-mentioned plasmid pW6AHCV core 120-120.

By use of this plasmid, Escherichia coli BL21 (DE3) was subjected to transformation, so that an ampicillin-resistant transformed Escherichia coli BL21 (DE3)/pW6AHCV core 120NA120 for expressing 120-fused 120NA (hereinafter referred to as 120NA120) was obtained.

EXAMPLE 8

[Purification of Insoluble 120NA120]

In the same manner as in Reference Example 2, the transformed Escherichia coli BL21 (DE3)/pW6AHCV core 120NA120 prepared in Example 7 was cultured overnight in an LB culture medium at 37° C. The optical density (OD) of the culture medium was adjusted by preculture so as to have about 0.7 when measured with light with a wavelength of 600 nm. Expression induction was then carried out with the addition of 0.5 mM IPTG thereto, and the cultivation was continued for two hours and 30 minutes.

The Escherichia coli cultivation medium was then centrifuged, whereby the Escherichia coli was collected. To the thus collected Escherichia coli, 150 ml of a buffer solution (50 mM tris-HCl, pH 8.0, 20% ethanol, 0.2 M NaCl, 0.3% OTG) was added, and the mixture was ice-cooled and subjected to ultrasonic disruption.

This mixture was then centrifuged, whereby an expressed 120NA120 was obtained as a soluble fraction as well as an insoluble fraction. The insoluble 120NA120 fraction was made soluble by a buffer solution (6M urea, 50 mM glycine-NaOH, pH 11.0) and was then subjected to centrifugation, whereby a supernatant fraction was obtained.

The thus obtained supernatant fraction was subjected to ion exchange purification, using an SFF cationic ion exchange column (made by Pharmacia Co., Ltd.) which was equilibrated with a buffer solution (6M urea-glycine-NaOH, pH 11.0), with sodium chloride elution. 120NA120 was recovered in an about 0.5M sodium chloride elution fraction.

The SFF eluted fraction was then purified, using Superdex 200 (gel filtration column)(made by Pharmacia Co., Ltd.) which was equilibrated with a buffer solution (6M urea-0.5M NaCl, 50 mM tris-HCl, pH 9.6). Thus, a purified 120NA120 was obtained in a portion with a molecular weight of about 40 kDa.

The nucleotide sequence and the amino acid sequence of the 120NA120 are respectively shown with Sequence ID. No. 11 and Sequence ID. No. 12 in the attached sequence table.

EXAMPLE 9

[Purification of Soluble Nucleic Acid-bound 120NA120 (120NA120(+)]

In the same manner as in Example 3, the Escherichia coli BL21 (DE3)/pW6AHCV core 120NA120 prepared in Example 7 was cultured overnight in an LB culture medium at 37° C. The optical density (OD) of the culture medium was adjusted by preculture so as to be about 0.7 when measured with light with a wavelength of 600 nm. Expression induction was then carried out with the addition of 0.5 mM IPTG thereto, and thereafter the cultivation was continued for two hours and 30 minutes.

The Escherichia coli cultivation medium was centrifuged, whereby the Escherichia coli was collected. To the thus collected Escherichia coli, 150 ml of a buffer solution (50 mM tris-HCl, pH 8.0, 20% ethanol, 0.2 M NaCl, 0.3% OTG) was added, and the mixture was ice-cooled and subjected to ultrasonic disruption.

This mixture was then centrifuged, whereby a soluble nucleic acid-bound 120NA120 (hereinafter referred to as "120NA120(+)") was recovered.

A 50%-sucrose concentration buffer solution was prepared by adding sucrose to a buffer solution (50 mM tris-HCl, pH 8.0, 20% ethanol) in such a manner that the concentration of sucrose in the buffer solution was 50%. In the same manner as mentioned above, a 30%-sucrose concentration buffer solution, and a 20%-sucrose concentration buffer solution were prepared.

These buffer solutions were overlaid in an ultracentrifuge tube in the direction from the bottom to the top portion of the tube in the order of the 50%-sucrose concentration buffer solution, the 30%-sucrose concentration buffer solution and the 20%-sucrose concentration buffer solution.

The 120NA120(+) containing soluble fraction was overlaid on top of the overlaid buffer solutions in the ultracentrifuge tube, and was then subjected to a first sucrose density gradient ultracentrifugation at 10° C., with a centrifugal force of 100,000 g, for 12 hours, using a Beckman ultrasonic centrifuge.

The 120NA120(+) was recovered in a portion with a sucrose concentration of about 30 to 40%.

The 120NA120(+) containing fraction recovered by the first sucrose density gradient ultracentrifugation was purified by Superdex 200 (gel filtration column) (made by Pharmacia Co., Ltd.) which was equilibrated with a buffer solution (0.3 M NaCl, 0.3% OTG, 50 mM glycine-NaOH, pH 10.0), whereby 120NA120(+) with a molecular weight of about 700 to 1000 kDa was recovered.

A 50%-sucrose concentration buffer solution was prepared by adding sucrose to a buffer solution (50 mM tris-HCl, pH 8.0, 20% ethanol) in such a manner that the concentration of sucrose in the buffer solution was 50%. In the same manner as mentioned above, a 20%-sucrose concentration buffer solution was prepared.

These buffer solutions were overlaid in an ultracentrifuge tube in the direction from the bottom to the top portion of the tube in the order of the 50%-sucrose concentration buffer solution and the 20%-sucrose concentration buffer solution.

The above-mentioned 120NA120(+) with a molecular weight of about 700 to 1000 kDa was overlaid on top of the overlaid buffer solutions in the ultracentrifuge tube, and was then subjected to a second sucrose density gradient centrifugation at 10° C., with a centrifugal force of 100,000 g, for 12 hours, using the Beckman ultrasonic centrifuge, whereby the 120NA120(+) was concentrated and purified.

EXAMPLE 10
[Rearrangement of 120NA120 to 120NA120(+)]

The OD 260/280 nm ratio of the 120NA120 purified in Example 9 was about 0.7.

To the purified 120NA120, there was added a purified DNA (about 1.3 to 0.7 Kbp)(made by Sigma Co., Ltd.), which was obtained form calf thymus and was subjected to sufficient cleavage by a restriction endonuclease Hae3. Furthermore, 6M urea, 20% sucrose and 1.0 M NaCl were added thereto.

This mixture was dialyzed against a buffer (50 mM tris-HCl, 0.3 M NaCl) at 4° C., whereby the 120NA120 was rearranged to a soluble 120NA120(+).

The soluble 120NA120(+) was purified by Superdex 200 (gel filtration column)(made by Pharmacia Co., Ltd.), whereby a purified 120NA120(+) was recovered in a portion with a molecular weight of about 700 to 1000 kDa. The OD 260/280 nm ratio of the thus recovered rearranged 120NA120(+) was about 1.8.

EXAMPLE 11
[Construction of Transformed *Escherichia coli* BL21 (DE3)/pW6A47C2NA for Expressing Nucleic Acid-Binding TP47 (TP47C2NA)]

A DNA fragment for coding a 47 kDa antigen derived from TP (*Treponema pallidum*), with Sequence ID No. 13 in the attached sequence table, was amplified by the PCR method, using as a template molecule a plasmid pW6A47C2 with a DNA fragment including a TP47 kDa antigen region being introduced, and was then digested with a restriction endonuclease EcoRI and a restriction endonuclease BamH.

A TP47 kDa antigen region-including DNA fragment 1.3 Kbp was separated by 1% agarose gel electrophoresis. This DNA fragment was inserted into an EcoRI-BamHI site of the expression plasmid pW6A shown in FIG. 1, whereby a plasmid pW6A47C2(EcoRI/BamHI) was prepared.

A DNA fragment for coding a HBc nucleic acid-binding motif with Sequence ID No. 1 in the attached sequence table was amplified by the PCR method, using as a template molecule a plasmid pHBV-11, and was then digested with a restriction endonuclease HamHI and a restriction endonuclease HindIII.

A nucleic acid-binding motif-containing DNA fragment 110 bp was then separated by 1% agarose gel electrophoresis. This DNA fragment was inserted into a BamHI-HindIII site of the above plasmid pW6A47C2 (EcoRI/BamHI).

By use of this plasmid, *Escherichia coli* BL21 (DE3) was subjected to transformation, so that an ampicillin-resistant transformed *Escherichia coli* BL21 (DE3)/pW6A47C2NA for expressing a nucleic acid-binding TP47 (hereinafter referred to as TP47C2NA) was obtained.

EXAMPLE 12
[Purification of Insoluble TP47C2NA]

In the same manner as in Reference Example 2, the transformed *Escherichia coli* BL21 (DE3)/pW6ATP47C2NA prepared in Example 11 was cultured overnight in an LB culture medium at 37° C. The optical density (OD) of the culture medium was adjusted by preculture so as to have about 0.7 when measured with light with a wavelength of 600 nm. Expression induction was then carried out with the addition of 0.5 mM IPTG thereto, and the cultivation was continued for two hours and 30 minutes.

The *Escherichia coli* cultivation medium was then centrifuged, whereby the *Escherichia coli* was collected. To the thus collected *Escherichia coli*, 150 ml of a buffer solution (50 mM tris-HCl, pH 8.0, 20% ethanol) was added, and the mixture was ice-cooled and subjected to ultrasonic disruption.

This mixture was then centrifuged, whereby an expressed TP47C2NA was obtained as a soluble fraction as well as an insoluble fraction. The insoluble TP47C2NA fraction was made soluble by a buffer solution (6M urea, 50 mM tris-HCl, pH 8.0) and was then subjected to centrifugation, whereby a supernatant fraction was obtained.

The thus obtained supernatant fraction was subjected to ion exchange purification, using an SFF cationic ion exchange column (made by Pharmacia Co., Ltd.) which was equilibrated with a buffer solution (8M urea, sodium acetate, pH 6.0), with sodium chloride elution. TP47C2NA was recovered in an about 0.5M sodium chloride elution fraction.

The SFF eluted fraction was then purified, using Superdex 200 (gel filtration column)(made by Pharmacia Co., Ltd.) which was equilibrated with a buffer solution (6M urea-0.5M NaCl, 50 mM tris-HCl, pH 9.6). Thus, a purified TP47C2NA was obtained in a portion with a molecular weight of about 100 kDa.

The nucleotide sequence and the amino acid sequence of the TP47C2NA are respectively shown with Sequence ID No. 15 and Sequence ID No. 16 in the attached sequence table.

EXAMPLE 13
[Purification of Soluble Nucleic Acid-bound TP47C2NA (TP47C2NA(+)]

In the same manner as in Example 3, the *Eacherichia coli* BL21 (DE3)/pW6ATP47C2NA prepared in Example 11 was cultured overnight in an LB culture medium at 37° C. The optical density (OD) of the culture medium was adjusted by preculture so as to be about 0.7 when measured with light with a wavelength of 600 nm. Expression induction was then carried out with the addition of 0.5 mM IPTG thereto, and thereafter the cultivation was continued for two hours and 30 minutes.

The *Escherichia coli* cultivation medium was centrifuged, whereby the *Escherichia coli* was collected. To the thus collected *Escherichia coli*, 150 ml of a buffer solution (50 mM tris-HCl, pH 8.0, 20% ethanol, 0.3% OTG) was added, and the mixture was ice-cooled and subjected to ultrasonic disruption.

This mixture was then centrifuged, whereby a soluble nucleic acid-bound TP47C2NA (hereinafter referred to as "TP47C2NA(+)") was recovered.

A 50%-sucrose concentration buffer solution was prepared by adding sucrose to a buffer solution (50 mM tris-HCl, pH 8.0, 20% ethanol) in such a manner that the concentration of sucrose in the buffer solution was 50%. In the same manner as mentioned above, a 30%-sucrose concentration buffer solution, and a 20%-sucrose concentration buffer solution were prepared.

These buffer solutions were overlaid in an ultracentrifuge tube in the direction from the bottom to the top portion of the tube in the order of the 50%-sucrose concentration buffer solution, the 30%-sucrose concentration buffer solution and the 20%-sucrose concentration buffer solution.

The TP47C2NA(+) containing soluble fraction was overlaid on top of the overlaid buffer solutions in the ultracentrifuge tube, and was then subjected to a first sucrose density gradient ultracentrifugation at 10° C., with a centrifugal force of 100,000 g, for 12 hours, using a Beckman ultrasonic centrifuge.

The TP47C2NA(+) was recovered in a portion with a sucrose concentration of about 30 to 45%.

The TP47C2NA(+) containing fraction recovered by the first sucrose density gradient ultracentrifugation was purified by Superdex 200 (gel filtration column) (made by Pharmacia Co., Ltd.) which was equilibrated with a buffer solution (0.3 M NaCl, 0.3% OTG, 50 mM glycine-NaOH, pH 10.0), whereby TP47C2NA(+) was recovered in a portion with a molecular weight of about 700 to 1000 kDa.

A 50%-sucrose concentration buffer solution was prepared by adding sucrose to a buffer solution (50 mM tris-HCl, pH 8.0, 20% ethanol) in such a manner that the concentration of sucrose in the buffer solution was 50%. In the same manner as mentioned above, a 20%-sucrose concentration buffer solution was prepared.

These buffer solutions were overlaid in an ultracentrifuge tube in the direction from the bottom to the top portion of the tube in the order of the 50%-sucrose concentration buffer solution and the 20%-sucrose concentration buffer solution.

The above-mentioned TP47C2NA(+) with a molecular weight of about 700 to 1000 kDa was overlaid on top of the overlaid buffer solutions in the ultracentrifuge tube, and was then subjected to a second sucrose density gradient centrifugation at 10° C., with a centrifugal force of 100,000 g, for 12 hours, using the Beckman ultrasonic centrifuge, whereby the TP47C2NA(+) was concentrated and purified.

EXAMPLE 14
[Rearrangement of TP47C2NA to TP47C2NA(+)]

The OD 260/280 nm ratio of the TP47C2NA purified in Example 12 was about 0.6.

To the purified TP47C2NA, there was added a purified DNA (about 1.3 to 0.7 Kbp)(made by Sigma Co., Ltd.), which was obtained form calf thymus and was subjected to sufficient cleavage by a restriction endonuclease Hae3. Furthermore, 6M urea, 20% sucrose and 1.0 M NaCl were added thereto.

This mixture was dialyzed against a buffer (50 mM tris-HCl, 0.3 M NaCl) at 4° C., whereby the TP47C2NA was rearranged to a soluble TP47C2NA(+).

The soluble TP47C2NA(+) was purified by Superdex 200 (gel filtration column) (made by Pharmacia Co., Ltd.), whereby a purified 120NA120(+) was recovered in a portion with a molecular weight of about 700 to 1000 kDa. The OD 260/280 nm ratio of the thus recovered rearranged TP47C2NA(+) was about 1.8.

EXAMPLE 15
[Construction of Transformed *Escherichia coli* BL21 (DE3)/pW6ACV Core 120pro1 for Expressing Mouse Protamine 1 fused 120 (120pro1)]

A DNA fragment for coding a mouse protamine 1 with Sequence ID No. 17 in the attached sequence table was isolated, and amplified by the PCR method, using as a template molecule a mouse protamine 1 cDNA, and was then digested with a restriction endonuclease EcoRI and a restriction endonuclease BamH.

A mouse protamine 1 region-including DNA fragment 160 bp was separated by 1% agarose gel electrophoresis. This DNA fragment was inserted into an EcoRI-BamHI site of the plasmid pW6AHCV core 120 (NheI/EcoRI) prepared in Example 1.

By use of this plasmid, *Escherichia coli* BL21 (DE3) was subjected to transformation, so that an ampicillin-resistant transformed *Escherichia coli* BL21 (DE3)/pW6ACV core 120pro1 for expressing a mouse protamine 1 fused 120 (hereinafter referred to as 120pro1) was obtained.

EXAMPLE 16
[Purification of 120pro1]

In the same manner as in Reference Example 2, the transformed *Escherichia coli* BL21 (DE3)/pW6AHCV core 120pro1 prepared in Example 15 was cultured overnight in an LB culture medium at 37° C. The optical density (OD) of the culture medium was adjusted by preculture so as to have about 0.7 when measured with light with a wavelength of 600 nm. Expression induction was then carried out with the addition of 0.5 mM IPTG thereto, and the cultivation was continued for 2 hours and 30 minutes.

The *Escherichia coli* cultivation medium was then centrifuged, whereby the *Escherichia coli* was collected. To the thus collected *Escherichia coli*, 150 ml of a buffer solution (50 mM tris-HCl, pH 8.0, 20% ethanol) was added, and the mixture was ice-cooled and subjected to ultrasonic disruption.

This mixture was then centrifuged, whereby an expressed 120pro1 was obtained as a soluble fraction as well as an insoluble fraction. The insoluble 120pro1 fraction was made soluble by a buffer solution (6M urea, 50 mM glycine-NaOH, pH 11.0) and was then subjected to centrifugation, whereby a supernatant fraction was obtained.

The thus obtained supernatant fraction was subjected to ion exchange purification, using an SFF cationic ion exchange column (made by Pharmacia Co., Ltd.) which was equilibrated with a buffer solution (6M urea-glycine-NaOH, pH 11.0), with sodium chloride elution. 120pro1 was recovered in an about 0.5M sodium chloride elution fraction.

The SFF eluted fraction was then purified, using Superdex 200 (gel filtration column)(made by Pharmacia Co., Ltd.) which was equilibrated with a buffer solution (6M urea-0.5M NaCl, 50 mM tris-HCl, pH 9.6). Thus, a purified 120pro1 was obtained in a portion with a molecular weight of about 22 kDa.

The nucleotide sequence and the amino acid sequence of the 120pro1 are respectively shown with Sequence ID No. 19 and Sequence ID No. 20 in the attached sequence table.

EXAMPLE 17
[Rearrangement of 120pro1 to 120pro1(+)]

The OD 260/280 nm ratio of the 120pro1 purified in Example 16 was about 0.7.

To the purified 120pro1, there was added a purified DNA (about 1.3 to 0.7 Kbp)(made by Sigma Co., Ltd.), which was obtained form calf thymus and was subjected to sufficient cleavage by a restriction endonuclease Hae3. Furthermore, 6M urea, 20% sucrose and 1.0 M NaCl were added thereto.

This mixture was dialyzed against a buffer (50 mM tris-HCl, 0.3M NaCl) at 4° C., whereby the 120pro1 was rearranged to a soluble 120pro1 (+).

The soluble 120pro1 (+) was purified by Superdex 200 (gel filtration column) (made by Pharmacia Co., Ltd.), whereby a purified 120pro1 (+) was recovered in a portion with a molecular weight of about 700 to 1000 kDa. The OD 260/280 nm ratio of the thus recovered rearranged 120pro1 (+) was about 1.7.

Thus, the present invention provides the nucleic acid-bound polypeptide with various properties of the polypeptide being changed, without changing the antigenicity thereof. The use of the nucleic acid-bound polypeptide of the present invention makes it possible to perform immunoassays which have been conventionally impossible.

Furthermore, according to the present invention, there is provided a method of recovering a genetic product in a soluble fraction, which has conventionally been recovered in an insoluble fraction.

Japanese Patent Application No. 8-134444 filed May 1, 1996, is hereby incorporated by reference.

What is claimed is:

1. An agglutination immunoassay comprising a polypeptide, wherein said immunoassay comprises:
   (a) preparing a nucleic acid-bound polypeptide by binding a nucleic acid to said polypeptide through a nucleic acid-binding motif in said polypeptide, and fixing said nucleic acid-bound polypeptide on the surface of particles;
   (b) contacting the particles obtained in (a) with a sample, wherein said sample may contain an antibody to an antigen, wherein said antigen is said polypeptide fixed on the surface of solid particles; and
   (c) measuring agglutination images of said particles caused by formation of antigen-antibody complex wherein said nucleic acid is bound to at least one terminus of said polypeptide, and
   wherein said nucleic acid-bound polypeptide further comprises a nucleic acid-binding motif through which said nucleic acid is bound to at least one terminus of said polypeptide.

2. The agglutination immunoassay as claimed in claim 1, wherein said polypeptide and said nucleic acid-binding motif are expressed in the form of a fusion polypeptide by genetic engineering.

3. The agglutination immunoassay according to claim 1, wherein said nucleic acid-binding motif has an amino acid sequence as set forth in SEQ ID NO. 2.

* * * * *

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH: 102 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic DNA"

(ix) FEATURE:
      (A) NAME/KEY: CDS
      (B) LOCATION: 1..102

(xi) SEQUENCE DESCRIPTION: SEQ ID NO: 1:

```
AGA CGA CGA GGG AGG TCC CCT AGA AGA AGA ACT CCC TCG CCT CGC AGA      48
Arg Arg Arg Gly Arg Ser Pro Arg Arg Arg Thr Pro Ser Pro Arg Arg
 1               5                  10                  15

CGA AGG TCT AAA TCG CCG CGT CGC AGA AGA TCT CAA TCT CGG GAA TCT      96
Arg Arg Ser Lys Ser Pro Arg Arg Arg Ser Gln Ser Arg Glu Ser
             20                  25                  30

CAA TGT                                                             102
Gln Cys
```

(2) INFORMATION FOR SEQ ID NO: 2:

(i) SEQUENCE CHARACTERISTICS:
      (A) LENGTH: 34 amino acids
      (B) TYPE: amino acid
      (D) TOPOLOGY: linear (ii) MOLECULE TYPE: protein (xi) SEQUENCE DESCRIPTION: SEQ ID NO: 2:

```
Arg Arg Arg Gly Arg Ser Pro Arg Arg Arg Thr Pro Ser Pro Arg Arg
 1               5                  10                  15

Arg Arg Ser Lys Ser Pro Arg Arg Arg Ser Gln Ser Arg Glu Ser
             20                  25                  30

Gln Cys
```

(2) INFORMATION FOR SEQ ID NO: 3:

(i) SEQUENCE CHARACTERISTICS:
      (A) LENGTH: 360 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic DNA"

(ix) FEATURE:
      (A) NAME/KEY: CDS
      (B) LOCATION: 1..360

(xi) SEQUENCE DESCRIPTION: SEQ ID NO: 3:

```
ATG AGC ACA AAT CCT AAA CCT CAA AGA AAA ACC AAA CGT AAC ACC AAC      48
Met Ser Thr Asn Pro Lys Pro Gln Arg Lys Thr Lys Arg Asn Thr Asn
 1               5                  10                  15

CGC CGC CCA CAG GAC GTT AAG TTC CCG GGC GGT GGT CAG ATC GTT GGT      96
```

```
Arg Arg Pro Gln Asp Val Lys Phe Pro Gly Gly Gln Ile Val Gly
         20                  25                  30

GGA GTT TAC CTG TTG CCG CGC AGG GGC CCC AGG TTG GGT GTG CGC GCG         144
Gly Val Tyr Leu Leu Pro Arg Arg Gly Pro Arg Leu Gly Val Arg Ala
         35                  40                  45

ACT AGG AAG ACT TCC GAG CGG TCG CAA CCT CGT GGA AGG CGA CAA CCT         192
Thr Arg Lys Thr Ser Glu Arg Ser Gln Pro Arg Gly Arg Arg Gln Pro
     50                  55                  60

ATC CCC AAG GCT CGC CGG CCC GAG GGT AGG ACC TGG GCT CAG CCC GGG         240
Ile Pro Lys Ala Arg Arg Pro Glu Gly Arg Thr Trp Ala Gln Pro Gly
 65                  70                  75                  80

TAC CCT TGG CCC CTC TAT GGC AAC GAG GGT ATG GGG TGG GCA GGA TGG         288
Tyr Pro Trp Pro Leu Tyr Gly Asn Glu Gly Met Gly Trp Ala Gly Trp
                 85                  90                  95

CTC CTG TCA CCC CGT GGC TCT CGG CCT AGT TGG GGC CCC ACA GAC CCC         336
Leu Leu Ser Pro Arg Gly Ser Arg Pro Ser Trp Gly Pro Thr Asp Pro
            100                 105                 110

CGG CGT AGG TCG CGT AAT TTG GGT                                         360
Arg Arg Arg Ser Arg Asn Leu Gly
            115                 120

(2) INFORMATION FOR SEQ ID NO: 4:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO: 4:

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
     50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Met Gly Trp Ala Gly Trp
                 85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly
            115                 120

(2) INFORMATION FOR SEQ ID NO: 5:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: CDS
        (B) LOCATION: 1..450
```

(xi) SEQUENCE DESCRIPTION: SEQ ID NO: 5:

```
ATG AGC ACA AAT CCT AAA CCT CAA AGA AAA ACC AAA CGT AAC ACC AAC         48
Met Ser Thr Asn Pro Lys Pro Gln Arg Lys Thr Lys Arg Asn Thr Asn
 1               5                  10                  15

CGC CGC CCA CGG GAC GTT AAA TTC CCG GGC GGT GGT CAG ATC GTT GGT         96
Arg Arg Pro Arg Asp Val Lys Phe Pro Gly Gly Gly Gln Ile Val Gly
                20                  25                  30

GGA GTT TAC CTG TTG CCG CGC AGG GGC CCC AGG TTG GGT GTG CGC GCG        144
Gly Val Tyr Leu Leu Pro Arg Arg Gly Pro Arg Leu Gly Val Arg Ala
            35                  40                  45

ACT AGG AAG ACT TCC GAG CGG TCG CAA CCT CGT GGA AGG CGA CAA CCT        192
Thr Arg Lys Thr Ser Glu Arg Ser Gln Pro Arg Gly Arg Arg Gln Pro
        50                  55                  60

ATC CCC AAG GCT CGC CGG CCC GAG GGT AGG ACC TGG GCT CAG CCC GGG        240
Ile Pro Lys Ala Arg Arg Pro Glu Gly Arg Thr Trp Ala Gln Pro Gly
65                  70                  75                  80

TAC CCT TGG CCC CTC TAT GGC AAC GAG GGT ATG GGG TGG GCA GGA TGG        288
Tyr Pro Trp Pro Leu Tyr Gly Asn Glu Gly Met Gly Trp Ala Gly Trp
                85                  90                  95

CTC CTG TCA CCC CGT GGC TCC CGG CCT AGT TGG GGC CCC ACG GAC CCC        336
Leu Leu Ser Pro Arg Gly Ser Arg Pro Ser Trp Gly Pro Thr Asp Pro
            100                 105                 110

CGG CGT AGG TCA CGC AAT TTG GGT AAG GTC ATC GAT ACC CTC ACA TGC        384
Arg Arg Arg Ser Arg Asn Leu Gly Lys Val Ile Asp Thr Leu Thr Cys
        115                 120                 125

GGC TTC GCC GAC CTC ATG GGG TAC ATT CCG CTT GTC GGC GCC CCC CTA        432
Gly Phe Ala Asp Leu Met Gly Tyr Ile Pro Leu Val Gly Ala Pro Leu
130                 135                 140

GGG GGC GCT GCC AGG GCC                                                450
Gly Gly Ala Ala Arg Ala
145                 150
```

(2) INFORMATION FOR SEQ ID NO: 6:

(i) SEQUENCE CHARACTERISTICS:
        (A) LENGTH: 150 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Ser Thr Asn Pro Lys Pro Gln Arg Lys Thr Lys Arg Asn Thr Asn
 1               5                  10                  15

Arg Arg Pro Arg Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
```

```
              130              135             140
Gly Gly Ala Ala Arg Ala
145                 150

(2) INFORMATION FOR SEQ ID NO: 7:

(i) SEQUENCE CHARACTERISTICS:
        (A) LENGTH: 483 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: CDS
        (B) LOCATION: 1..483

(xi) SEQUENCE DESCRIPTION: SEQ ID NO: 7:

ATG GCT AGC GAA TTC ATG AGC ACA AAT CCT AAA CCT CAA AGA AAA ACC        48
Met Ala Ser Glu Phe Met Ser Thr Asn Pro Lys Pro Gln Arg Lys Thr
 1               5                  10                  15

AAA CGT AAC ACC AAC CGC CGC CCA CAG GAC GTT AAG TTC CCG GGC GGT        96
Lys Arg Asn Thr Asn Arg Arg Pro Gln Asp Val Lys Phe Pro Gly Gly
                20                  25                  30

GGT CAG ATC GTT GGT GGA GTT TAC CTG TTG CCG CGC AGG GGC CCC AGG       144
Gly Gln Ile Val Gly Gly Val Tyr Leu Leu Pro Arg Arg Gly Pro Arg
            35                  40                  45

TTG GGT GTG CGC GCG ACT AGG AAG ACT TCC GAG CGG TCG CAA CCT CGT       192
Leu Gly Val Arg Ala Thr Arg Lys Thr Ser Glu Arg Ser Gln Pro Arg
        50                  55                  60

GGA AGG CGA CAA CCT ATC CCC AAG GCT CGC CGG CCC GAG GGT AGG ACC       240
Gly Arg Arg Gln Pro Ile Pro Lys Ala Arg Arg Pro Glu Gly Arg Thr
 65                  70                  75                  80

TGG GCT CAG CCC GGG TAC CCT TGG CCC CTC TAT GGC AAC GAG GGT ATG       288
Trp Ala Gln Pro Gly Tyr Pro Trp Pro Leu Tyr Gly Asn Glu Gly Met
                 85                  90                  95

GGG TGG GCA GGA TGG CTC CTG TCA CCC CGT GGC TCT CGG CCT AGT TGG       336
Gly Trp Ala Gly Trp Leu Leu Ser Pro Arg Gly Ser Arg Pro Ser Trp
            100                 105                 110

GGC CCC ACA GAC CCC CGG CGT AGG TCG CGT AAT TTG GGT GGA TCC AGA       384
Gly Pro Thr Asp Pro Arg Arg Arg Ser Arg Asn Leu Gly Gly Ser Arg
        115                 120                 125

CGA CGA GGC AGG TCC CCT AGA AGA AGA ACT CCC TCG CCT CGC AGA CGA       432
Arg Arg Gly Arg Ser Pro Arg Arg Arg Thr Pro Ser Pro Arg Arg Arg
    130                 135                 140

AGG TCT AAA TCG CCG CGT CGC AGA AGA TCT CAA TCT CGG GAA TCT CAA       480
Arg Ser Lys Ser Pro Arg Arg Arg Ser Gln Ser Arg Glu Ser Gln
145                 150                 155                 160

TGT                                                                   483
Cys (2) INFORMATION FOR SEQ ID NO: 8:

(i) SEQUENCE CHARACTERISTICS:
        (A) LENGTH: 161 amino acids
        (B) TYPE: amino acid
        (D) TOPOLOGY: linear (ii) MOLECULE TYPE: protein (xi) SEQUENCE DESCRIPTION: SEQ ID NO: 8:

Met Ala Ser Glu Phe Met Ser Thr Asn Pro Lys Pro Gln Arg Lys Thr
```

```
                1               5              10              15
              Lys Arg Asn Thr Asn Arg Arg Pro Gln Asp Val Lys Phe Pro Gly Gly
                              20              25              30

Gly Gln Ile Val Gly Gly Val Tyr Leu Leu Pro Arg Arg Gly Pro Arg
                              35              40              45

Leu Gly Val Arg Ala Thr Arg Lys Thr Ser Glu Arg Ser Gln Pro Arg
                              50              55              60

Gly Arg Arg Gln Pro Ile Pro Lys Ala Arg Arg Pro Glu Gly Arg Thr
               65             70              75              80

Trp Ala Gln Pro Gly Tyr Pro Trp Pro Leu Tyr Gly Asn Glu Gly Met
                              85              90              95

Gly Trp Ala Gly Trp Leu Leu Ser Pro Arg Gly Ser Arg Pro Ser Trp
                              100             105             110

Gly Pro Thr Asp Pro Arg Arg Ser Arg Asn Leu Gly Gly Ser Arg
                              115             120             125

Arg Arg Gly Arg Ser Pro Arg Arg Thr Pro Ser Pro Arg Arg Arg
               130             135             140

Arg Ser Lys Ser Pro Arg Arg Arg Ser Gln Ser Arg Glu Ser Gln
              145              150             155             160

Cys (2) INFORMATION FOR SEQ ID NO: 9:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: CDS
        (B) LOCATION: 1..573

(xi) SEQUENCE DESCRIPTION: SEQ ID NO: 9:

ATG GCT AGC GAA TTC ATG AGC ACA AAT CCT AAA CCT CAA AGA AAA ACC        48
Met Ala Ser Glu Phe Met Ser Thr Asn Pro Lys Pro Gln Arg Lys Thr
 1               5                  10                  15

AAA CGT AAC ACC AAC CGC CGC CCA CGG GAC GTT AAA TTC CCG GGC GGT        96
Lys Arg Asn Thr Asn Arg Arg Pro Arg Asp Val Lys Phe Pro Gly Gly
                20                  25                  30

GGT CAG ATC GTT GGT GGA GTT TAC CTG TTG CCG CGC AGG GGC CCC AGG       144
Gly Gln Ile Val Gly Gly Val Tyr Leu Leu Pro Arg Arg Gly Pro Arg
                35                  40                  45

TTG GGT GTG CGC GCG ACT AGG AAG ACT TCC GAG CGG TCG CAA CCT CGT       192
Leu Gly Val Arg Ala Thr Arg Lys Thr Ser Glu Arg Ser Gln Pro Arg
                50                  55                  60

GGA AGG CGA CAA CCT ATC CCC AAG GCT CGC CGG CCC GAG GGT AGG ACC       240
Gly Arg Arg Gln Pro Ile Pro Lys Ala Arg Arg Pro Glu Gly Arg Thr
 65                 70                  75                  80

TGG GCT CAG CCC GGG TAC CCT TGG CCC CTC TAT GGC AAC GAG GGT ATG       288
Trp Ala Gln Pro Gly Tyr Pro Trp Pro Leu Tyr Gly Asn Glu Gly Met
                85                  90                  95

GGG TGG GCA GGA TGG CTC CTG TCA CCC CGT GGC TCC CGG CCT AGT TGG       336
Gly Trp Ala Gly Trp Leu Leu Ser Pro Arg Gly Ser Arg Pro Ser Trp
                100                 105                 110

GGC CCC ACG GAC CCC CGG CGT AGG TCA CGC AAT TTG GGT AAG GTC ATC       384
Gly Pro Thr Asp Pro Arg Arg Arg Ser Arg Asn Leu Gly Lys Val Ile
```

|       |       |       |       | 115   |       |       |       |       | 120   |       |       |       |       | 125   |       |       |     |
|-------|-------|-------|-------|-------|-------|-------|-------|-------|-------|-------|-------|-------|-------|-------|-------|-------|-----|
| GAT   | ACC   | CTC   | ACA   | TGC   | GGC   | TTC   | GCC   | GAC   | CTC   | ATG   | GGG   | TAC   | ATT   | CCG   | CTT   |       | 432 |
| Asp   | Thr   | Leu   | Thr   | Cys   | Gly   | Phe   | Ala   | Asp   | Leu   | Met   | Gly   | Tyr   | Ile   | Pro   | Leu   |       |     |
|       | 130   |       |       |       |       | 135   |       |       |       |       | 140   |       |       |       |       |       |     |

GTC GGC GCC CCC CTA GGG GGC GCT GCC AGG GCC GGA TCC AGA CGA CGA    480
Val Gly Ala Pro Leu Gly Gly Ala Ala Arg Ala Gly Ser Arg Arg Arg
145             150                 155                 160

GGC AGG TCC CCT AGA AGA AGA ACT CCC TCG CCT CGC AGA CGA AGG TCT    528
Gly Arg Ser Pro Arg Arg Arg Thr Pro Ser Pro Arg Arg Arg Ser
            165                 170                 175

AAA TCG CCG CGT CGC AGA AGA TCT CAA TCT CGG GAA TCT CAA TGT        573
Lys Ser Pro Arg Arg Arg Ser Gln Ser Arg Glu Ser Gln Cys
        180                 185                 190

(2) INFORMATION FOR SEQ ID NO: 10:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO: 10:

Met Ala Ser Glu Phe Met Ser Thr Asn Pro Lys Pro Gln Arg Lys Thr
1               5                   10                  15

Lys Arg Asn Thr Asn Arg Arg Pro Arg Asp Val Lys Phe Pro Gly Gly
                20                  25                  30

Gly Gln Ile Val Gly Gly Val Tyr Leu Leu Pro Arg Arg Gly Pro Arg
            35                  40                  45

Leu Gly Val Arg Ala Thr Arg Lys Thr Ser Glu Arg Ser Gln Pro Arg
        50                  55                  60

Gly Arg Arg Gln Pro Ile Pro Lys Ala Arg Arg Pro Glu Gly Arg Thr
65                  70                  75                  80

Trp Ala Gln Pro Gly Tyr Pro Trp Pro Leu Tyr Gly Asn Glu Gly Met
                85                  90                  95

Gly Trp Ala Gly Trp Leu Leu Ser Pro Arg Gly Ser Arg Pro Ser Trp
            100                 105                 110

Gly Pro Thr Asp Pro Arg Arg Arg Ser Arg Asn Leu Gly Lys Val Ile
        115                 120                 125

Asp Thr Leu Thr Cys Gly Phe Ala Asp Leu Met Gly Tyr Ile Pro Leu
    130                 135                 140

Val Gly Ala Pro Leu Gly Gly Ala Ala Arg Ala Gly Ser Arg Arg Arg
145             150                 155                 160

Gly Arg Ser Pro Arg Arg Arg Thr Pro Ser Pro Arg Arg Arg Ser
            165                 170                 175

Lys Ser Pro Arg Arg Arg Ser Gln Ser Arg Glu Ser Gln Cys
        180                 185                 190

(2) INFORMATION FOR SEQ ID NO: 11:

(i) SEQUENCE CHARACTERISTICS:
        (A) LENGTH: 843 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:

(A) NAME/KEY: CDS
(B) LOCATION: 1..843

(xi) SEQUENCE DESCRIPTION: SEQ ID NO: 11:

| | | | | | | | | | | | | | | | | |
|---|---|---|---|---|---|---|---|---|---|---|---|---|---|---|---|---|
| ATG | GCT | AGC | ATG | AGC | ACA | AAT | CCT | AAA | CCT | CAA | AGA | AAA | ACC | AAA | CGT | 48 |
| Met | Ala | Ser | Met | Ser | Thr | Asn | Pro | Lys | Pro | Gln | Arg | Lys | Thr | Lys | Arg | |
| 1 | | | | 5 | | | | | 10 | | | | | 15 | | |
| AAC | ACC | AAC | CGC | CGC | CCA | CAG | GAC | GTT | AAG | TTC | CCG | GGC | GGT | GGT | CAG | 96 |
| Asn | Thr | Asn | Arg | Arg | Pro | Gln | Asp | Val | Lys | Phe | Pro | Gly | Gly | Gly | Gln | |
| | | | 20 | | | | | 25 | | | | | 30 | | | |
| ATC | GTT | GGT | GGA | GTT | TAC | CTG | TTG | CCG | CGC | AGG | GGC | CCC | AGG | TTG | GGT | 144 |
| Ile | Val | Gly | Gly | Val | Tyr | Leu | Leu | Pro | Arg | Arg | Gly | Pro | Arg | Leu | Gly | |
| | | 35 | | | | | 40 | | | | | 45 | | | | |
| GTG | CGC | GCG | ACT | AGG | AAG | ACT | TCC | GAG | CGG | TCG | CAA | CCT | CGT | GGA | AGG | 192 |
| Val | Arg | Ala | Thr | Arg | Lys | Thr | Ser | Glu | Arg | Ser | Gln | Pro | Arg | Gly | Arg | |
| | 50 | | | | | 55 | | | | | 60 | | | | | |
| CGA | CAA | CCT | ATC | CCC | AAG | GCT | CGC | CGG | CCC | GAG | GGT | AGG | ACC | TGG | GCT | 240 |
| Arg | Gln | Pro | Ile | Pro | Lys | Ala | Arg | Arg | Pro | Glu | Gly | Arg | Thr | Trp | Ala | |
| 65 | | | | 70 | | | | | 75 | | | | | 80 | | |
| CAG | CCC | GGG | TAC | CCT | TGG | CCC | CTC | TAT | GGC | AAC | GAG | GGT | ATG | GGG | TGG | 288 |
| Gln | Pro | Gly | Tyr | Pro | Trp | Pro | Leu | Tyr | Gly | Asn | Glu | Gly | Met | Gly | Trp | |
| | | | | 85 | | | | | 90 | | | | | 95 | | |
| GCA | GGA | TGG | CTC | CTG | TCA | CCC | CGT | GGC | TCT | CGG | CCT | AGT | TGG | GGC | CCC | 336 |
| Ala | Gly | Trp | Leu | Leu | Ser | Pro | Arg | Gly | Ser | Arg | Pro | Ser | Trp | Gly | Pro | |
| | | | 100 | | | | | 105 | | | | | 110 | | | |
| ACA | GAC | CCC | CGG | CGT | AGG | TCG | CGT | AAT | TTG | GGT | GAA | TTC | AGA | CGA | CGA | 384 |
| Thr | Asp | Pro | Arg | Arg | Arg | Ser | Arg | Asn | Leu | Gly | Glu | Phe | Arg | Arg | Arg | |
| | | | 115 | | | | | 120 | | | | | 125 | | | |
| GGC | AGG | TCC | CCT | AGA | AGA | AGA | ACT | CCC | TCG | CCT | CGC | AGA | CGA | AGG | TCT | 432 |
| Gly | Arg | Ser | Pro | Arg | Arg | Arg | Thr | Pro | Ser | Pro | Arg | Arg | Arg | Arg | Ser | |
| | 130 | | | | | 135 | | | | | 140 | | | | | |
| AAA | TCG | CCG | CGT | CGC | AGA | AGA | TCT | CAA | TCT | CGG | GAA | TCT | CAA | TGT | GAA | 480 |
| Lys | Ser | Pro | Arg | Arg | Arg | Arg | Ser | Gln | Ser | Arg | Glu | Ser | Gln | Cys | Glu | |
| 145 | | | | 150 | | | | | 155 | | | | | 160 | | |
| TTC | ATG | AGC | ACA | AAT | CCT | AAA | CCT | CAA | AGA | AAA | ACC | AAA | CGT | AAC | ACC | 528 |
| Phe | Met | Ser | Thr | Asn | Pro | Lys | Pro | Gln | Arg | Lys | Thr | Lys | Arg | Asn | Thr | |
| | | | | 165 | | | | | 170 | | | | | 175 | | |
| AAC | CGC | CGC | CCA | CAG | GAC | GTT | AAG | TTC | CCG | GGC | GGT | GGT | CAG | ATC | GTT | 576 |
| Asn | Arg | Arg | Pro | Gln | Asp | Val | Lys | Phe | Pro | Gly | Gly | Gly | Gln | Ile | Val | |
| | | | 180 | | | | | 185 | | | | | 190 | | | |
| GGT | GGA | GTT | TAC | CTG | TTG | CCG | CGC | AGG | GGC | CCC | AGG | TTG | GGT | GTG | CGC | 624 |
| Gly | Gly | Val | Tyr | Leu | Leu | Pro | Arg | Arg | Gly | Pro | Arg | Leu | Gly | Val | Arg | |
| | | 195 | | | | | 200 | | | | | 205 | | | | |
| GCG | ACT | AGG | AAG | ACT | TCC | GAG | CGG | TCG | CAA | CCT | CGT | GGA | AGG | CGA | CAA | 672 |
| Ala | Thr | Arg | Lys | Thr | Ser | Glu | Arg | Ser | Gln | Pro | Arg | Gly | Arg | Arg | Gln | |
| | 210 | | | | | 215 | | | | | 220 | | | | | |
| CCT | ATC | CCC | AAG | GCT | CGC | CGG | CCC | GAG | GGT | AGG | ACC | TGG | GCT | CAG | CCC | 720 |
| Pro | Ile | Pro | Lys | Ala | Arg | Arg | Pro | Glu | Gly | Arg | Thr | Trp | Ala | Gln | Pro | |
| 225 | | | | 230 | | | | | 235 | | | | | 240 | | |
| GGG | TAC | CCT | TGG | CCC | CTC | TAT | GGC | AAC | GAG | GGT | ATG | GGG | TGG | GCA | GGA | 768 |
| Gly | Tyr | Pro | Trp | Pro | Leu | Tyr | Gly | Asn | Glu | Gly | Met | Gly | Trp | Ala | Gly | |
| | | | | 245 | | | | | 250 | | | | | 255 | | |
| TGG | CTC | CTG | TCA | CCC | CGT | GGC | TCT | CGG | CCT | AGT | TGG | GGC | CCC | ACA | GAC | 816 |
| Trp | Leu | Leu | Ser | Pro | Arg | Gly | Ser | Arg | Pro | Ser | Trp | Gly | Pro | Thr | Asp | |
| | | | 260 | | | | | 265 | | | | | 270 | | | |
| CCC | CGG | CGT | AGG | TCG | CGT | AAT | TTG | GGT | | | | | | | | 843 |
| Pro | Arg | Arg | Arg | Ser | Arg | Asn | Leu | Gly | | | | | | | | |
| | | | 275 | | | | | 280 | | | | | | | | |

(2) INFORMATION FOR SEQ ID NO: 12:

(i) SEQUENCE CHARACTERISTICS:
    (A) LENGTH: 281 amino acids
    (B) TYPE: amino acid
    (D) TOPOLOGY: linear (ii) MOLECULE TYPE: protein (xi) SEQUENCE DESCRIPTION: SEQ ID NO: 12:

```
Met Ala Ser Met Ser Thr Asn Pro Lys Pro Gln Arg Lys Thr Lys Arg
  1               5                  10                  15

Asn Thr Asn Arg Arg Pro Gln Asp Val Lys Phe Pro Gly Gly Gly Gln
             20                  25                  30

Ile Val Gly Gly Val Tyr Leu Leu Pro Arg Arg Gly Pro Arg Leu Gly
             35                  40                  45

Val Arg Ala Thr Arg Lys Thr Ser Glu Arg Ser Gln Pro Arg Gly Arg
 50                  55                  60

Arg Gln Pro Ile Pro Lys Ala Arg Arg Pro Glu Gly Arg Thr Trp Ala
 65                  70                  75                  80

Gln Pro Gly Tyr Pro Trp Pro Leu Tyr Gly Asn Glu Gly Met Gly Trp
                 85                  90                  95

Ala Gly Trp Leu Leu Ser Pro Arg Gly Ser Arg Pro Ser Trp Gly Pro
                100                 105                 110

Thr Asp Pro Arg Arg Arg Ser Arg Asn Leu Gly Glu Phe Arg Arg Arg
                115                 120                 125

Gly Arg Ser Pro Arg Arg Arg Thr Pro Ser Pro Arg Arg Arg Arg Ser
130                 135                 140

Lys Ser Pro Arg Arg Arg Ser Gln Ser Arg Glu Ser Gln Cys Glu
145                 150                 155                 160

Phe Met Ser Thr Asn Pro Lys Pro Gln Arg Lys Thr Lys Arg Asn Thr
                165                 170                 175

Asn Arg Arg Pro Gln Asp Val Lys Phe Pro Gly Gly Gly Gln Ile Val
            180                 185                 190

Gly Gly Val Tyr Leu Leu Pro Arg Arg Gly Pro Arg Leu Gly Val Arg
            195                 200                 205

Ala Thr Arg Lys Thr Ser Glu Arg Ser Gln Pro Arg Gly Arg Arg Gln
            210                 215                 220

Pro Ile Pro Lys Ala Arg Arg Pro Glu Gly Arg Thr Trp Ala Gln Pro
225                 230                 235                 240

Gly Tyr Pro Trp Pro Leu Tyr Gly Asn Glu Gly Met Gly Trp Ala Gly
                245                 250                 255

Trp Leu Leu Ser Pro Arg Gly Ser Arg Pro Ser Trp Gly Pro Thr Asp
            260                 265                 270

Pro Arg Arg Arg Ser Arg Asn Leu Gly
            275                 280
```

(2) INFORMATION FOR SEQ ID NO: 13:

(i) SEQUENCE CHARACTERISTICS:
        (A) LENGTH: 1245 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: CDS
        (B) LOCATION: 1..1245

(xi) SEQUENCE DESCRIPTION: SEQ ID NO: 13:

| | | | | | | | | | | | | | | | | |
|---|---|---|---|---|---|---|---|---|---|---|---|---|---|---|---|---|
| ATG | GGC | TCG | TCT | CAT | CAT | GAG | ACG | CAC | TAT | GGC | TAT | GCG | ACG | CTA | AGC | 48 |
| Met | Gly | Ser | Ser | His | His | Glu | Thr | His | Tyr | Gly | Tyr | Ala | Thr | Leu | Ser | |
| 1 | | | | 5 | | | | | 10 | | | | | 15 | | |
| TAT | GCG | GAC | TAC | TGG | GCC | GGG | GAG | TTG | GGG | CAG | AGT | AGG | GAC | GTG | CTT | 96 |
| Tyr | Ala | Asp | Tyr | Trp | Ala | Gly | Glu | Leu | Gly | Gln | Ser | Arg | Asp | Val | Leu | |
| | | | 20 | | | | | 25 | | | | | 30 | | | |
| TTG | GCG | GGT | AAT | GCC | GAG | GCG | GAC | CGC | GCG | GGG | GAT | CTC | GAC | GCA | GGC | 144 |
| Leu | Ala | Gly | Asn | Ala | Glu | Ala | Asp | Arg | Ala | Gly | Asp | Leu | Asp | Ala | Gly | |
| | | 35 | | | | | 40 | | | | | 45 | | | | |
| ATG | TTC | GAT | GCA | GTT | TCT | CGC | GCA | ACC | CAC | GGG | CAT | GGC | GCG | TTC | CGT | 192 |
| Met | Phe | Asp | Ala | Val | Ser | Arg | Ala | Thr | His | Gly | His | Gly | Ala | Phe | Arg | |
| 50 | | | | | 55 | | | | | 60 | | | | | | |
| CAG | CAA | TTT | CAG | TAC | GCG | GTT | GAG | GTA | TTG | GGC | GAA | AAG | GTT | CTC | TCG | 240 |
| Gln | Gln | Phe | Gln | Tyr | Ala | Val | Glu | Val | Leu | Gly | Glu | Lys | Val | Leu | Ser | |
| 65 | | | | 70 | | | | | 75 | | | | | 80 | | |
| AAG | CAG | GAG | ACC | GAA | GAC | AGC | AGG | GGA | AGA | AAA | AAG | TGG | GAG | TAC | GAG | 288 |
| Lys | Gln | Glu | Thr | Glu | Asp | Ser | Arg | Gly | Arg | Lys | Lys | Trp | Glu | Tyr | Glu | |
| | | | | 85 | | | | | 90 | | | | | 95 | | |
| ACT | GAC | CCA | AGC | GTT | ACT | AAG | ATG | GTG | CGT | GCC | TCT | GCG | TCA | TTT | CAG | 336 |
| Thr | Asp | Pro | Ser | Val | Thr | Lys | Met | Val | Arg | Ala | Ser | Ala | Ser | Phe | Gln | |
| | | | 100 | | | | | 105 | | | | | 110 | | | |
| GAT | TTG | GGA | GAG | GAC | GGG | GAG | ATT | AAG | TTT | GAA | GCA | GTC | GAG | GGT | GCA | 384 |
| Asp | Leu | Gly | Glu | Asp | Gly | Glu | Ile | Lys | Phe | Glu | Ala | Val | Glu | Gly | Ala | |
| | | 115 | | | | | 120 | | | | | 125 | | | | |
| GTA | GCG | TTG | GCG | GAT | CGC | GCG | AGT | TCC | TTC | ATG | GTT | GAC | AGC | GAG | GAA | 432 |
| Val | Ala | Leu | Ala | Asp | Arg | Ala | Ser | Ser | Phe | Met | Val | Asp | Ser | Glu | Glu | |
| 130 | | | | | 135 | | | | | 140 | | | | | | |
| TAC | AAG | ATT | ACG | AAC | GTA | AAG | GTT | CAC | GGT | ATG | AAG | TTT | GTC | CCA | GTT | 480 |
| Tyr | Lys | Ile | Thr | Asn | Val | Lys | Val | His | Gly | Met | Lys | Phe | Val | Pro | Val | |
| 145 | | | | | 150 | | | | | 155 | | | | | 160 | |
| GCG | GTT | CCT | CAT | GAA | TTA | AAA | GGG | ATT | GCA | AAG | GAG | AAG | TTT | CAC | TTC | 528 |
| Ala | Val | Pro | His | Glu | Leu | Lys | Gly | Ile | Ala | Lys | Glu | Lys | Phe | His | Phe | |
| | | | | 165 | | | | | 170 | | | | | 175 | | |
| GTG | GAA | GAC | TCC | CGC | GTT | ACG | GAG | AAT | ACC | AAC | GGC | CTT | AAG | ACA | ATG | 576 |
| Val | Glu | Asp | Ser | Arg | Val | Thr | Glu | Asn | Thr | Asn | Gly | Leu | Lys | Thr | Met | |
| | | | 180 | | | | | 185 | | | | | 190 | | | |
| CTC | ACT | GAG | GAT | AGT | TTT | TCT | GCA | CGT | AAG | GTA | AGC | AGC | ATG | GAG | AGC | 624 |
| Leu | Thr | Glu | Asp | Ser | Phe | Ser | Ala | Arg | Lys | Val | Ser | Ser | Met | Glu | Ser | |
| | | 195 | | | | | 200 | | | | | 205 | | | | |
| CCG | CAC | GAC | CTT | GTG | GTA | GAC | ACG | GTG | GGT | ACC | GTC | TAC | CAC | AGC | CGT | 672 |
| Pro | His | Asp | Leu | Val | Val | Asp | Thr | Val | Gly | Thr | Val | Tyr | His | Ser | Arg | |
| 210 | | | | | 215 | | | | | 220 | | | | | | |
| TTT | GGT | TCG | GAC | GCA | GAG | GCT | TCT | GTG | ATG | CTG | AAA | AGG | GCT | GAT | GGC | 720 |
| Phe | Gly | Ser | Asp | Ala | Glu | Ala | Ser | Val | Met | Leu | Lys | Arg | Ala | Asp | Gly | |
| 225 | | | | | 230 | | | | | 235 | | | | | 240 | |
| TCT | GAG | CTG | TCG | CAC | CGT | GAG | TTC | ATC | GAC | TAT | GTG | ATG | AAC | TTC | AAC | 768 |
| Ser | Glu | Leu | Ser | His | Arg | Glu | Phe | Ile | Asp | Tyr | Val | Met | Asn | Phe | Asn | |
| | | | | 245 | | | | | 250 | | | | | 255 | | |
| ACG | GTC | CGC | TAC | GAC | TAC | TAC | GGT | GAT | GAC | GCG | AGC | TAC | ACC | AAT | CTG | 816 |
| Thr | Val | Arg | Tyr | Asp | Tyr | Tyr | Gly | Asp | Asp | Ala | Ser | Tyr | Thr | Asn | Leu | |
| | | | 260 | | | | | 265 | | | | | 270 | | | |
| ATG | GCG | AGT | TAT | GGC | ACC | AAG | CAC | TCT | GCT | GAC | TCC | TGG | TGG | AAG | ACA | 864 |
| Met | Ala | Ser | Tyr | Gly | Thr | Lys | His | Ser | Ala | Asp | Ser | Trp | Trp | Lys | Thr | |
| | | 275 | | | | | 280 | | | | | 285 | | | | |
| GGA | AGA | GTG | CCC | CGC | ATT | TCG | TGT | GGT | ATC | AAC | TAT | GGG | TTC | GAT | CGG | 912 |
| Gly | Arg | Val | Pro | Arg | Ile | Ser | Cys | Gly | Ile | Asn | Tyr | Gly | Phe | Asp | Arg | |
| 290 | | | | | 295 | | | | | 300 | | | | | | |

-continued

```
TTT AAA GGT TCA GGG CCG GGA TAC TAC AGG CTG ACT TTG ATT GCG AAC      960
Phe Lys Gly Ser Gly Pro Gly Tyr Tyr Arg Leu Thr Leu Ile Ala Asn
305                 310                 315                 320

GGG TAT AGG GAC GTA GTT GCT GAT GTG CGC TTC CTT CCC AAG TAC GAG     1008
Gly Tyr Arg Asp Val Val Ala Asp Val Arg Phe Leu Pro Lys Tyr Glu
                325                 330                 335

GGG AAC ATC GAT ATT GGG TTG AAG GGG AAG GTG CTG ACC ATA GGG GGC     1056
Gly Asn Ile Asp Ile Gly Leu Lys Gly Lys Val Leu Thr Ile Gly Gly
            340                 345                 350

GCG GAC GCG GAG ACT CTG ATG GAT GCT GCA GTT GAC GTG TTT GCC GAT     1104
Ala Asp Ala Glu Thr Leu Met Asp Ala Ala Val Asp Val Phe Ala Asp
        355                 360                 365

GGA CAG CCT AAG CTT GTC AGC GAT CAA GCG GTG AGC TTG GGG CAG AAT     1152
Gly Gln Pro Lys Leu Val Ser Asp Gln Ala Val Ser Leu Gly Gln Asn
370                 375                 380

GTC CTC TCT GCG GAT TTC ACT CCC GGC ACT GAG TAC ACG GTT GAG GTT     1200
Val Leu Ser Ala Asp Phe Thr Pro Gly Thr Glu Tyr Thr Val Glu Val
385                 390                 395                 400

AGG TTC AAG GAA TTT GGT TCT GTG CGT GCG AAG GTA GTG GCC CAG         1245
Arg Phe Lys Glu Phe Gly Ser Val Arg Ala Lys Val Val Ala Gln
                405                 410                 415
```

(2) INFORMATION FOR SEQ ID NO: 14:

(i) SEQUENCE CHARACTERISTICS:
        (A) LENGTH: 415 amino acids
        (B) TYPE: amino acid
        (D) TOPOLOGY: linear (ii) MOLECULE TYPE: protein (xi) SEQUENCE DESCRIPTION: SEQ ID NO: 14:

```
Met Gly Ser Ser His His Glu Thr His Tyr Gly Tyr Ala Thr Leu Ser
1               5                   10                  15

Tyr Ala Asp Tyr Trp Ala Gly Glu Leu Gly Gln Ser Arg Asp Val Leu
                20                  25                  30

Leu Ala Gly Asn Ala Glu Ala Asp Arg Ala Gly Asp Leu Asp Ala Gly
            35                  40                  45

Met Phe Asp Ala Val Ser Arg Ala Thr His Gly His Gly Ala Phe Arg
        50                  55                  60

Gln Gln Phe Gln Tyr Ala Val Glu Val Leu Gly Glu Lys Val Leu Ser
65                  70                  75                  80

Lys Gln Glu Thr Glu Asp Ser Arg Gly Arg Lys Lys Trp Glu Tyr Glu
                85                  90                  95

Thr Asp Pro Ser Val Thr Lys Met Val Arg Ala Ser Ala Ser Phe Gln
                100                 105                 110

Asp Leu Gly Glu Asp Gly Glu Ile Lys Phe Glu Ala Val Glu Gly Ala
            115                 120                 125

Val Ala Leu Ala Asp Arg Ala Ser Ser Phe Met Val Asp Ser Glu Glu
        130                 135                 140

Tyr Lys Ile Thr Asn Val Lys Val His Gly Met Lys Phe Val Pro Val
145                 150                 155                 160

Ala Val Pro His Glu Leu Lys Gly Ile Ala Lys Glu Lys Phe His Phe
                165                 170                 175

Val Glu Asp Ser Arg Val Thr Glu Asn Thr Asn Gly Leu Lys Thr Met
            180                 185                 190

Leu Thr Glu Asp Ser Phe Ser Ala Arg Lys Val Ser Ser Met Glu Ser
        195                 200                 205
```

```
Pro His Asp Leu Val Val Asp Thr Val Gly Thr Val Tyr His Ser Arg
    210                 215                 220

Phe Gly Ser Asp Ala Glu Ala Ser Val Met Leu Lys Arg Ala Asp Gly
225                 230                 235                 240

Ser Glu Leu Ser His Arg Glu Phe Ile Asp Tyr Val Met Asn Phe Asn
                245                 250                 255

Thr Val Arg Tyr Asp Tyr Tyr Gly Asp Asp Ala Ser Tyr Thr Asn Leu
            260                 265                 270

Met Ala Ser Tyr Gly Thr Lys His Ser Ala Asp Ser Trp Trp Lys Thr
        275                 280                 285

Gly Arg Val Pro Arg Ile Ser Cys Gly Ile Asn Tyr Gly Phe Asp Arg
    290                 295                 300

Phe Lys Gly Ser Gly Pro Gly Tyr Tyr Arg Leu Thr Leu Ile Ala Asn
305                 310                 315                 320

Gly Tyr Arg Asp Val Val Ala Asp Val Arg Phe Leu Pro Lys Tyr Glu
                325                 330                 335

Gly Asn Ile Asp Ile Gly Leu Lys Gly Lys Val Leu Thr Ile Gly Gly
            340                 345                 350

Ala Asp Ala Glu Thr Leu Met Asp Ala Ala Val Asp Val Phe Ala Asp
        355                 360                 365

Gly Gln Pro Lys Leu Val Ser Asp Gln Ala Val Ser Leu Gly Gln Asn
370                 375                 380

Val Leu Ser Ala Asp Phe Thr Pro Gly Thr Glu Tyr Thr Val Glu Val
385                 390                 395                 400

Arg Phe Lys Glu Phe Gly Ser Val Arg Ala Lys Val Val Ala Gln
                405                 410                 415

(2) INFORMATION FOR SEQ ID NO: 15:

(i) SEQUENCE CHARACTERISTICS:
        (A) LENGTH: 1368 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: CDS
        (B) LOCATION: 1..1368

(xi) SEQUENCE DESCRIPTION: SEQ ID NO: 15:

ATG GCT AGC GAA TTC ATG GGC TCG TCT CAT CAT GAG ACG CAC TAT GGC      48
Met Ala Ser Glu Phe Met Gly Ser Ser His His Glu Thr His Tyr Gly
1               5                   10                  15

TAT GCG ACG CTA AGC TAT GCG GAC TAC TGG GCC GGG GAG TTG GGG CAG      96
Tyr Ala Thr Leu Ser Tyr Ala Asp Tyr Trp Ala Gly Glu Leu Gly Gln
            20                  25                  30

AGT AGG GAC GTG CTT TTG GCG GGT AAT GCC GAG GCG GAC CGC GCG GGG     144
Ser Arg Asp Val Leu Leu Ala Gly Asn Ala Glu Ala Asp Arg Ala Gly
        35                  40                  45

GAT CTC GAC GCA GGC ATG TTC GAT GCA GTT TCT CGC GCA ACC CAC GGG     192
Asp Leu Asp Ala Gly Met Phe Asp Ala Val Ser Arg Ala Thr His Gly
    50                  55                  60

CAT GGC GCG TTC CGT CAG CAA TTT CAG TAC GCG GTT GAG GTA TTG GGC     240
His Gly Ala Phe Arg Gln Gln Phe Gln Tyr Ala Val Glu Val Leu Gly
65                  70                  75                  80

GAA AAG GTT CTC TCG AAG CAG GAG ACC GAA GAC AGC AGG GGA AGA AAA     288
Glu Lys Val Leu Ser Lys Gln Glu Thr Glu Asp Ser Arg Gly Arg Lys
```

```
                    85                  90                  95
AAG TGG GAG TAC GAG ACT GAC CCA AGC GTT ACT AAG ATG GTG CGT GCC      336
Lys Trp Glu Tyr Glu Thr Asp Pro Ser Val Thr Lys Met Val Arg Ala
                100                 105                 110

TCT GCG TCA TTT CAG GAT TTG GGA GAG GAC GGG GAG ATT AAG TTT GAA      384
Ser Ala Ser Phe Gln Asp Leu Gly Glu Asp Gly Glu Ile Lys Phe Glu
            115                 120                 125

GCA GTC GAG GGT GCA GTA GCG TTG GCG GAT CGC GCG AGT TCC TTC ATG      432
Ala Val Glu Gly Ala Val Ala Leu Ala Asp Arg Ala Ser Ser Phe Met
        130                 135                 140

GTT GAC AGC GAG GAA TAC AAG ATT ACG AAC GTA AAG GTT CAC GGT ATG      480
Val Asp Ser Glu Glu Tyr Lys Ile Thr Asn Val Lys Val His Gly Met
145                 150                 155                 160

AAG TTT GTC CCA GTT GCG GTT CCT CAT GAA TTA AAA GGG ATT GCA AAG      528
Lys Phe Val Pro Val Ala Val Pro His Glu Leu Lys Gly Ile Ala Lys
                165                 170                 175

GAG AAG TTT CAC TTC GTG GAA GAC TCC CGC GTT ACG GAG AAT ACC AAC      576
Glu Lys Phe His Phe Val Glu Asp Ser Arg Val Thr Glu Asn Thr Asn
            180                 185                 190

GGC CTT AAG ACA ATG CTC ACT GAG GAT AGT TTT TCT GCA CGT AAG GTA      624
Gly Leu Lys Thr Met Leu Thr Glu Asp Ser Phe Ser Ala Arg Lys Val
        195                 200                 205

AGC AGC ATG GAG AGC CCG CAC GAC CTT GTG GTA GAC ACG GTG GGT ACC      672
Ser Ser Met Glu Ser Pro His Asp Leu Val Val Asp Thr Val Gly Thr
210                 215                 220

GTC TAC CAC AGC CGT TTT GGT TCG GAC GCA GAG GCT TCT GTG ATG CTG      720
Val Tyr His Ser Arg Phe Gly Ser Asp Ala Glu Ala Ser Val Met Leu
225                 230                 235                 240

AAA AGG GCT GAT GGC TCT GAG CTG TCG CAC CGT GAG TTC ATC GAC TAT      768
Lys Arg Ala Asp Gly Ser Glu Leu Ser His Arg Glu Phe Ile Asp Tyr
                245                 250                 255

GTG ATG AAC TTC AAC ACG GTC CGC TAC GAC TAC TAC GGT GAT GAC GCG      816
Val Met Asn Phe Asn Thr Val Arg Tyr Asp Tyr Tyr Gly Asp Asp Ala
            260                 265                 270

AGC TAC ACC AAT CTG ATG GCG AGT TAT GGC ACC AAG CAC TCT GCT GAC      864
Ser Tyr Thr Asn Leu Met Ala Ser Tyr Gly Thr Lys His Ser Ala Asp
        275                 280                 285

TCC TGG TGG AAG ACA GGA AGA GTG CCC CGC ATT TCG TGT GGT ATC AAC      912
Ser Trp Trp Lys Thr Gly Arg Val Pro Arg Ile Ser Cys Gly Ile Asn
290                 295                 300

TAT GGG TTC GAT CGG TTT AAA GGT TCA GGG CCG GGA TAC TAC AGG CTG      960
Tyr Gly Phe Asp Arg Phe Lys Gly Ser Gly Pro Gly Tyr Tyr Arg Leu
305                 310                 315                 320

ACT TTG ATT GCG AAC GGG TAT AGG GAC GTA GTT GCT GAT GTG CGC TTC     1008
Thr Leu Ile Ala Asn Gly Tyr Arg Asp Val Val Ala Asp Val Arg Phe
                325                 330                 335

CTT CCC AAG TAC GAG GGG AAC ATC GAT ATT GGG TTG AAG GGG AAG GTG     1056
Leu Pro Lys Tyr Glu Gly Asn Ile Asp Ile Gly Leu Lys Gly Lys Val
            340                 345                 350

CTG ACC ATA GGG GGC GCG GAC GCG GAG ACT CTG ATG GAT GCT GCA GTT     1104
Leu Thr Ile Gly Gly Ala Asp Ala Glu Thr Leu Met Asp Ala Ala Val
        355                 360                 365

GAC GTG TTT GCC GAT GGA CAG CCT AAG CTT GTC AGC GAT CAA GCG GTG     1152
Asp Val Phe Ala Asp Gly Gln Pro Lys Leu Val Ser Asp Gln Ala Val
370                 375                 380

AGC TTG GGG CAG AAT GTC CTC TCT GCG GAT TTC ACT CCC GGC ACT GAG     1200
Ser Leu Gly Gln Asn Val Leu Ser Ala Asp Phe Thr Pro Gly Thr Glu
385                 390                 395                 400

TAC ACG GTT GAG GTT AGG TTC AAG GAA TTT GGT TCT GTG CGT GCG AAG     1248
```

```
Tyr Thr Val Glu Val Arg Phe Lys Glu Phe Gly Ser Val Arg Ala Lys
                405                 410                 415

GTA GTG GCC CAG GGA TCC AGA CGA CGA GGC AGG TCC CCT AGA AGA AGA         1296
Val Val Ala Gln Gly Ser Arg Arg Arg Gly Arg Ser Pro Arg Arg Arg
                420                 425                 430

ACT CCC TCG CCT CGC AGA CGA AGG TCT AAA TCG CCG CGT CGC AGA AGA         1344
Thr Pro Ser Pro Arg Arg Arg Arg Ser Lys Ser Pro Arg Arg Arg Arg
                435                 440                 445

TCT CAA TCT CGG GAA TCT CAA TGT                                         1368
Ser Gln Ser Arg Glu Ser Gln Cys
        450                 455

(2) INFORMATION FOR SEQ ID NO: 16:

(i) SEQUENCE CHARACTERISTICS:
        (A) LENGTH: 456 amino acids
        (B) TYPE: amino acid
        (D) TOPOLOGY: linear (ii) MOLECULE TYPE: protein (xi) SEQUENCE DESCRIPTION: SEQ ID NO: 16:

Met Ala Ser Glu Phe Met Gly Ser Ser His His Glu Thr His Tyr Gly
 1               5                  10                  15

Tyr Ala Thr Leu Ser Tyr Ala Asp Tyr Trp Ala Gly Glu Leu Gly Gln
            20                  25                  30

Ser Arg Asp Val Leu Leu Ala Gly Asn Ala Glu Ala Asp Arg Ala Gly
        35                  40                  45

Asp Leu Asp Ala Gly Met Phe Asp Ala Val Ser Arg Ala Thr His Gly
    50                  55                  60

His Gly Ala Phe Arg Gln Gln Phe Gln Tyr Ala Val Glu Val Leu Gly
65                  70                  75                  80

Glu Lys Val Leu Ser Lys Gln Glu Thr Glu Asp Ser Arg Gly Arg Lys
                85                  90                  95

Lys Trp Glu Tyr Glu Thr Asp Pro Ser Val Thr Lys Met Val Arg Ala
            100                 105                 110

Ser Ala Ser Phe Gln Asp Leu Gly Glu Asp Gly Glu Ile Lys Phe Glu
        115                 120                 125

Ala Val Glu Gly Ala Val Ala Leu Ala Asp Arg Ala Ser Ser Phe Met
    130                 135                 140

Val Asp Ser Glu Glu Tyr Lys Ile Thr Asn Val Lys Val His Gly Met
145                 150                 155                 160

Lys Phe Val Pro Val Ala Val Pro His Glu Leu Lys Gly Ile Ala Lys
                165                 170                 175

Glu Lys Phe His Phe Val Glu Asp Ser Arg Val Thr Glu Asn Thr Asn
            180                 185                 190

Gly Leu Lys Thr Met Leu Thr Glu Asp Ser Phe Ser Ala Arg Lys Val
        195                 200                 205

Ser Ser Met Glu Ser Pro His Asp Leu Val Val Asp Thr Val Gly Thr
    210                 215                 220

Val Tyr His Ser Arg Phe Gly Ser Asp Ala Glu Ala Ser Val Met Leu
225                 230                 235                 240

Lys Arg Ala Asp Gly Ser Glu Leu Ser His Arg Glu Phe Ile Asp Tyr
                245                 250                 255

Val Met Asn Phe Asn Thr Val Arg Tyr Asp Tyr Tyr Gly Asp Asp Ala
            260                 265                 270

Ser Tyr Thr Asn Leu Met Ala Ser Tyr Gly Thr Lys His Ser Ala Asp
```

```
             275                 280                 285
Ser Trp Trp Lys Thr Gly Arg Val Pro Arg Ile Ser Cys Gly Ile Asn
    290                 295                 300

Tyr Gly Phe Asp Arg Phe Lys Gly Ser Gly Pro Gly Tyr Tyr Arg Leu
305                 310                 315                 320

Thr Leu Ile Ala Asn Gly Tyr Arg Asp Val Ala Asp Val Arg Phe
                325                 330                 335

Leu Pro Lys Tyr Glu Gly Asn Ile Asp Ile Gly Leu Lys Gly Lys Val
                340                 345                 350

Leu Thr Ile Gly Gly Ala Asp Ala Glu Thr Leu Met Asp Ala Ala Val
                355                 360                 365

Asp Val Phe Ala Asp Gly Gln Pro Lys Leu Val Ser Asp Gln Ala Val
370                 375                 380

Ser Leu Gly Gln Asn Val Leu Ser Ala Asp Phe Thr Pro Gly Thr Glu
385                 390                 395                 400

Tyr Thr Val Glu Val Arg Phe Lys Glu Phe Gly Ser Val Arg Ala Lys
                405                 410                 415

Val Val Ala Gln Gly Ser Arg Arg Gly Arg Ser Pro Arg Arg Arg
                420                 425                 430

Thr Pro Ser Pro Arg Arg Arg Ser Lys Ser Pro Arg Arg Arg Arg
                435                 440                 445

Ser Gln Ser Arg Glu Ser Gln Cys
    450                 455
```

(2) INFORMATION FOR SEQ ID NO: 17:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: CDS
        (B) LOCATION: 1..153

(xi) SEQUENCE DESCRIPTION: SEQ ID NO: 17:

```
ATG GCC AGA TAC CGA TGC TGC CGC AGC AAA AGC AGG AGC AGA TGC CGC        48
Met Ala Arg Tyr Arg Cys Cys Arg Ser Lys Ser Arg Ser Arg Cys Arg
  1               5                  10                  15

CGT CGC AGA CGA AGA TGT CGC AGA CGG AGG AGG CGA TGC TGC CGG CGG        96
Arg Arg Arg Arg Arg Cys Arg Arg Arg Arg Arg Cys Cys Arg Arg
                 20                  25                  30

AGG AGG CGA AGA TGC TGC CGT CGC CGC CGC TCA TAC ACC ATA AGG TGT       144
Arg Arg Arg Arg Cys Cys Arg Arg Arg Ser Tyr Thr Ile Arg Cys
             35                  40                  45

AAA AAA TAC                                                           153
Lys Lys Tyr
    50
```

(2) INFORMATION FOR SEQ ID NO: 18:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO: 18:

```
Met Ala Arg Tyr Arg Cys Cys Arg Ser Lys Ser Arg Ser Arg Cys Arg
 1               5                  10                  15

Arg Arg Arg Arg Arg Cys Arg Arg Arg Arg Arg Cys Cys Arg Arg
            20                  25                  30

Arg Arg Arg Arg Cys Cys Arg Arg Arg Ser Tyr Thr Ile Arg Cys
        35                  40                  45

Lys Lys Tyr
    50
```

(2) INFORMATION FOR SEQ ID NO: 19:

(i) SEQUENCE CHARACTERISTICS:
        (A) LENGTH: 528 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: CDS
        (B) LOCATION: 1..528

(xi) SEQUENCE DESCRIPTION: SEQ ID NO: 19:

```
ATG GCT AGC ATG AGC ACA AAT CCT AAA CCT CAA AGA AAA ACC AAA CGT        48
Met Ala Ser Met Ser Thr Asn Pro Lys Pro Gln Arg Lys Thr Lys Arg
 1               5                  10                  15

AAC ACC AAC CGC CGC CCA CGG GAC GTT AAA TTC CCG GGC GGT GGT CAG        96
Asn Thr Asn Arg Arg Pro Arg Asp Val Lys Phe Pro Gly Gly Gly Gln
            20                  25                  30

ATC GTT GGT GGA GTT TAC CTG TTG CCG CGC AGG GGC CCC AGG TTG GGT       144
Ile Val Gly Gly Val Tyr Leu Leu Pro Arg Arg Gly Pro Arg Leu Gly
        35                  40                  45

GTG CGC GCG ACT AGG AAG ACT TCC GAG CGG TCG CAA CCT CGT GGA AGG       192
Val Arg Ala Thr Arg Lys Thr Ser Glu Arg Ser Gln Pro Arg Gly Arg
    50                  55                  60

CGA CAA CCT ATC CCC AAG GCT CGC CGG CCC GAG GGT AGG ACC TGG GCT       240
Arg Gln Pro Ile Pro Lys Ala Arg Arg Pro Glu Gly Arg Thr Trp Ala
65                  70                  75                  80

CAG CCC GGG TAC CCT TGG CCC CTC TAT GGC AAC GAG GGT ATG GGG TGG       288
Gln Pro Gly Tyr Pro Trp Pro Leu Tyr Gly Asn Glu Gly Met Gly Trp
                85                  90                  95

GCA GGA TGG CTC CTG TCA CCC CGT GGC TCC CGG CCT AGT TGG GGC CCC       336
Ala Gly Trp Leu Leu Ser Pro Arg Gly Ser Arg Pro Ser Trp Gly Pro
            100                 105                 110

ACG GAC CCC CGG CGT AGG TCA CGC AAT TTG GGT GAA TTC ATG GCC AGA       384
Thr Asp Pro Arg Arg Arg Ser Arg Asn Leu Gly Glu Phe Met Ala Arg
        115                 120                 125

TAC CGA TGC TGC CGC AGC AAA AGC AGG AGC AGA TGC CGC CGT CGC AGA       432
Tyr Arg Cys Cys Arg Ser Lys Ser Arg Ser Arg Cys Arg Arg Arg Arg
    130                 135                 140

CGA AGA TGT CGC AGA CGG AGG AGG CGA TGC TGC CGG CGG AGG AGG CGA       480
Arg Arg Cys Arg Arg Arg Arg Arg Cys Cys Arg Arg Arg Arg Arg Arg
145                 150                 155                 160

AGA TGC TGC CGT CGC CGC CGC TCA TAC ACC ATA AGG TGT AAA AAA TAC       528
Arg Cys Cys Arg Arg Arg Arg Ser Tyr Thr Ile Arg Cys Lys Lys Tyr
                165                 170                 175
```

(2) INFORMATION FOR SEQ ID NO: 20:

-continued (i) SEQUENCE CHARACTERISTICS:
    (A) LENGTH: 176 amino acids
    (B) TYPE: amino acid
    (D) TOPOLOGY: linear (ii) MOLECULE TYPE: protein (xi) SEQUENCE DESCRIPTION: SEQ ID NO: 20:

```
Met Ala Ser Met Ser Thr Asn Pro Lys Pro Gln Arg Lys Thr Lys Arg
  1               5                  10                  15

Asn Thr Asn Arg Arg Pro Arg Asp Val Lys Phe Pro Gly Gly Gly Gln
                 20                  25                  30

Ile Val Gly Gly Val Tyr Leu Leu Pro Arg Arg Gly Pro Arg Leu Gly
             35                  40                  45

Val Arg Ala Thr Arg Lys Thr Ser Glu Arg Ser Gln Pro Arg Gly Arg
         50                  55                  60

Arg Gln Pro Ile Pro Lys Ala Arg Arg Pro Glu Gly Arg Thr Trp Ala
 65                  70                  75                  80

Gln Pro Gly Tyr Pro Trp Pro Leu Tyr Gly Asn Glu Gly Met Gly Trp
                 85                  90                  95

Ala Gly Trp Leu Leu Ser Pro Arg Gly Ser Arg Pro Ser Trp Gly Pro
                100                 105                 110

Thr Asp Pro Arg Arg Arg Ser Arg Asn Leu Gly Glu Phe Met Ala Arg
                115                 120                 125

Tyr Arg Cys Cys Arg Ser Lys Ser Arg Ser Arg Cys Arg Arg Arg Arg
130                 135                 140

Arg Arg Cys Arg Arg Arg Arg Arg Cys Cys Arg Arg Arg Arg Arg Arg
145                 150                 155                 160

Arg Cys Cys Arg Arg Arg Arg Ser Tyr Thr Ile Arg Cys Lys Lys Tyr
                165                 170                 175
```